(12) United States Patent
Bicek et al.

(10) Patent No.: US 12,254,165 B2
(45) Date of Patent: Mar. 18, 2025

(54) MONITORING AND MANAGEMENT OF WEARABLE DEVICES

(71) Applicant: Inviza LLC, Malden, MA (US)

(72) Inventors: Nicholas J. Bicek, Penfield, NY (US); Christopher H. Bicek, Penfield, NY (US); Theodore B. Ziemkowski, Firestone, CO (US); Peeraya Nilwong, Firestone, CO (US); Robert G. Andosca, Malden, MA (US)

(73) Assignee: Inviza Corporation, Cambridge, MA (US)

( * ) Notice: Subject to any disclaimer, the term of this patent is extended or adjusted under 35 U.S.C. 154(b) by 247 days.

(21) Appl. No.: 18/096,441

(22) Filed: Jan. 12, 2023

(65) Prior Publication Data

US 2023/0229284 A1   Jul. 20, 2023

Related U.S. Application Data

(60) Provisional application No. 63/300,971, filed on Jan. 19, 2022.

(51) Int. Cl.
| | |
|---|---|
| *G06F 3/04817* | (2022.01) |
| *A61B 5/00* | (2006.01) |
| *A61B 5/024* | (2006.01) |
| *G06F 3/04842* | (2022.01) |
| *G06F 3/0488* | (2022.01) |
| *G16H 40/67* | (2018.01) |

(52) U.S. Cl.
CPC ...... *G06F 3/04817* (2013.01); *A61B 5/02438* (2013.01); *A61B 5/7435* (2013.01); *A61B 5/7475* (2013.01); *G06F 3/04842* (2013.01); *G06F 3/0488* (2013.01); *G16H 40/67* (2018.01)

(58) Field of Classification Search
CPC .................................................. G06F 3/04817
USPC ......................................................... 715/834
See application file for complete search history.

(56) References Cited

U.S. PATENT DOCUMENTS

| | | | |
|---|---|---|---|
| 10,505,726 B1* | 12/2019 | Andon | H04L 9/0643 |
| 11,429,252 B2* | 8/2022 | Williams | A63B 24/0062 |
| 11,721,440 B1* | 8/2023 | Shan | G16H 40/67 705/2 |
| 12,050,854 B1* | 7/2024 | Shan | G06F 40/40 |
| 2014/0335795 A1* | 11/2014 | Wilbur | H04W 4/024 455/67.11 |
| 2016/0085415 A1* | 3/2016 | Humphrys | A61B 5/0205 715/846 |
| 2016/0165852 A1* | 6/2016 | Goldfain | G06F 3/0481 340/573.3 |

(Continued)

*Primary Examiner* — Reza Nabi
(74) *Attorney, Agent, or Firm* — Kaplan Breyer Schwarz, LLP

(57) ABSTRACT

Aspects of the present disclosure describe systems and methods that enable a user of a computing device (e.g., a smartphone, tablet, etc.) to interact with a wearable device worn by the user. In one embodiment, the computing device provides a touchscreen-based graphical user interface (GUI). The GUI displays a three-quarter view of a plurality of icons arranged in a ring, where each of the icons is associated with a respective health/fitness parameter (e.g., heart rate, blood oxygen saturation, etc.). The GUI enables the user to interact with the wearable device through the computing device, via swiping gestures, presses of icons, and press-and-holds of the icons.

20 Claims, 18 Drawing Sheets

(56) References Cited

U.S. PATENT DOCUMENTS

| | | | | |
|---|---|---|---|---|
| 2016/0174099 | A1* | 6/2016 | Goldfain | A61B 5/6831 |
| | | | | 375/130 |
| 2016/0206921 | A1* | 7/2016 | Szabados | G01P 15/00 |
| 2016/0241553 | A1* | 8/2016 | Kim | H04W 12/33 |
| 2017/0052747 | A1* | 2/2017 | Cervelli | G06T 11/001 |
| 2017/0076560 | A1* | 3/2017 | Dasilva | G06Q 10/06 |
| 2018/0267569 | A1* | 9/2018 | Wang | G06Q 20/3678 |
| 2019/0134463 | A1* | 5/2019 | Ma | A61B 5/6802 |
| 2019/0339860 | A1* | 11/2019 | Chen | G06F 1/163 |
| 2020/0163621 | A1* | 5/2020 | Connor | A61B 5/389 |
| 2021/0169417 | A1* | 6/2021 | Burton | A61B 5/4857 |
| 2022/0014120 | A1* | 1/2022 | Andosca | H10N 30/093 |
| 2022/0035367 | A1* | 2/2022 | Ho | G08G 5/0043 |
| 2022/0096006 | A1* | 3/2022 | Wu | A61B 5/1123 |
| 2022/0131482 | A1* | 4/2022 | Andosca | A43B 13/125 |
| 2022/0343444 | A1* | 10/2022 | Chan | G06F 16/353 |
| 2023/0155523 | A1* | 5/2023 | Andosca | H10N 30/098 |
| | | | | 36/136 |
| 2023/0194491 | A1* | 6/2023 | Huang | G01N 33/0036 |
| | | | | 73/23.2 |
| 2023/0229284 | A1* | 7/2023 | Bicek | G06F 3/04817 |
| 2023/0367472 | A1* | 11/2023 | Clarke | G06F 3/04842 |
| 2024/0028129 | A1* | 1/2024 | Whitmire | G06F 1/163 |
| 2024/0045217 | A1* | 2/2024 | Moll | G06F 3/167 |
| 2024/0070996 | A1* | 2/2024 | Gurgul | G06T 19/006 |

* cited by examiner

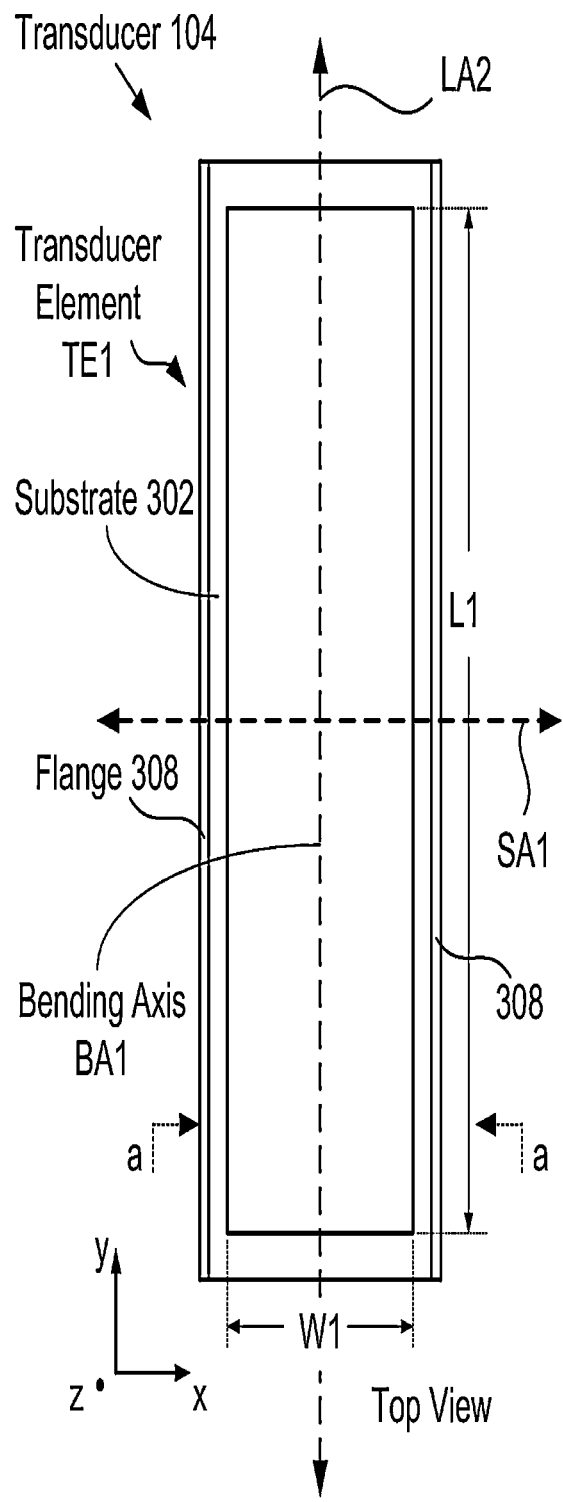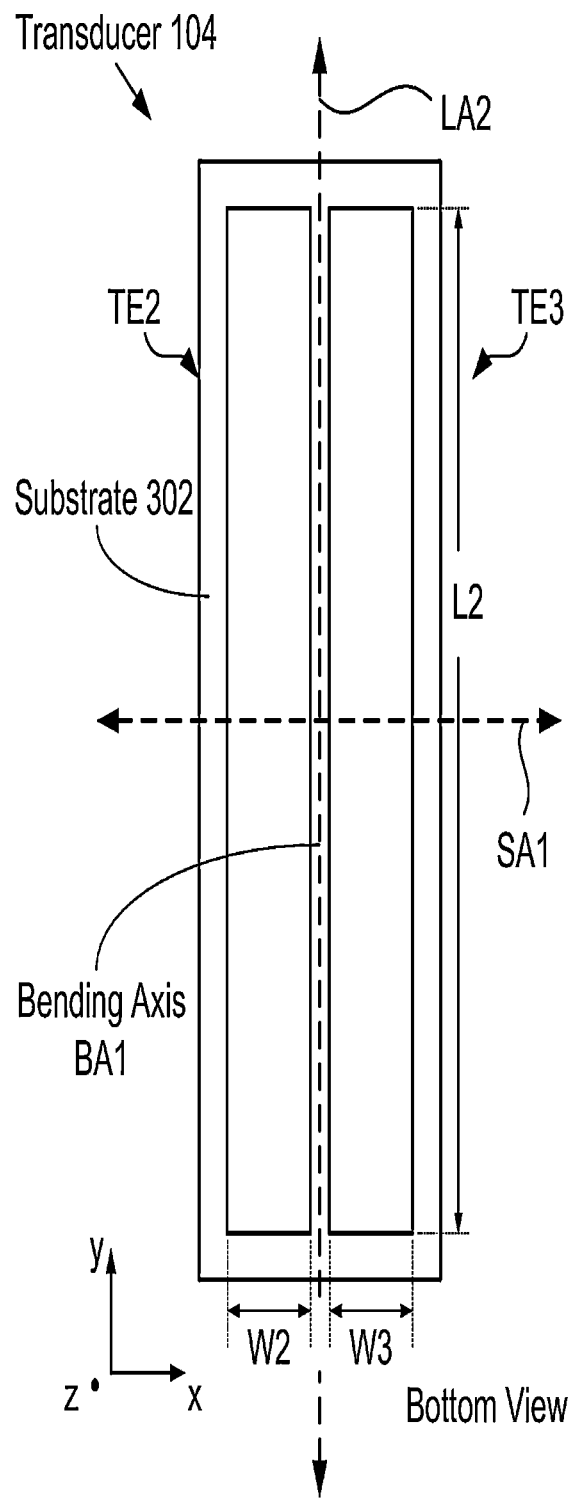
FIG. 3A
FIG. 3B

MONITORING AND MANAGEMENT OF WEARABLE DEVICES

CROSS REFERENCE TO RELATED APPLICATIONS

This application claims priority to, and incorporates fully by reference, U.S. Provisional Application Ser. No. 63/300,971, filed Jan. 19, 2022, entitled "Sensors for Smart Garments and Applications Thereof,". This application also incorporates by reference U.S. Pat. Ser. No. 17/373,690, entitled "Piezo-Elements for Wearable Devices,". If there are any contradictions or inconsistencies in language between this application and one or more of the cases that have been incorporated by reference that might affect the interpretation of the claims in this case, the claims in this case should be interpreted to be consistent with the language in this case.

TECHNICAL FIELD

The present disclosure relates to wearable devices in general, and, more particularly, to: (1) self-powered sensors and actuators suitable for inclusion in a wearable, such as smart clothing for use by humans and/or animals such as, garments, footwear, accessories, and the like; and (2) a graphical user interface (GUI) executing on a computing device (e.g., a smartphone, a tablet, a laptop computer, a desktop computer, etc.) through which to interact with one or more wearable devices.

BACKGROUND

Wearables, such as fitness trackers and smart watches have become increasingly popular over the past few years. These devices and systems have evolved to the point at which they can connect with other devices, like computers and smartphones, thereby enhancing their overall capabilities.

Unfortunately, one area that remains a challenge is providing power to wearables—particularly as more systems and sub-systems are included to augment their capabilities. For example, many contemporary wearables include rechargeable batteries. Unfortunately, rechargeable batteries must be frequently connected to a charging station of some sort, during which time the wearable is typically out of service.

Furthermore, the capacity of many rechargeable batteries (e.g. Lithium ion "Li+" or Lithium polymer "LiPo", etc.) degrades over time to a point where the wearable becomes inoperative.

The need for a self-powered wearable that requires little or no downtime for recharging remains, as yet, unmet in the prior art. In addition, there is a need for an elegant graphical user interface (GUI) for computing devices (e.g., smartphones, tablets, laptop computers, desktop computers, etc.) through which a user can interact with wearables.

SUMMARY

The present disclosure is directed toward self-powered wearables for users/subjects such as humans, animals, robotics, exoskeletons, and the like. Embodiments in accordance with the present disclosure are suitable for use in accessories and/or garments for humans, such as clothing, shoes, sandals, exercise equipment and clothing, cell phone cases, luggage (e.g., suitcases, backpacks, etc.), purses, undergarments (e.g., bras, socks, sole members (e.g., insoles, midsoles, outsoles, etc.), human-machine interfaces (e.g., joysticks, position-sensing-gloves, etc.), smart gloves, and the like, as well as garments and/or accessories for animals, such as horseshoes, leashes, collars, and the like.

Like the prior art, embodiments in accordance with the present disclosure include transducers that generate electrical energy in response to an applied force. In sharp contrast to the prior art, however, transducers disclosed herein have a quiescent shape that is curved (or "bent") about at least one bending axis. The transducers are configured to generate electrical energy when they are flattened relative to their bending axis (or axes) in response to the applied force, as well as when returning to their quiescent state upon removal of the applied force. Furthermore, transducers in accordance with the present disclosure are dimensioned and arranged to mitigate compression of their piezoelectric material by the applied force.

An advance over the prior art is realized by incorporating a transducer comprising a non-resonant energy harvester into a wearable to power one or more devices, such as sensors, haptic devices, wireless communication devices, and the like, such that the energy harvester generates electrical energy when it (1) "flattens" in response to the application of a force and/or returns to its non-flat quiescent state when the applied force is removed. By configuring the energy harvester such that it functions substantially as a bending-strain-based device, it can generate significantly more power than those known in the prior art. Furthermore, some energy harvesters in accordance with the present disclosure employ a low dielectric-constant (K) or "low-K" piezoelectric material, which enables high-voltage/power operation and/or a significantly thinner energy harvester or sensor transducer.

An illustrative embodiment in accordance with the present disclosure is a smart shoe insole comprising a processor, an energy storage unit, a wireless communications module, a geolocation module, and plurality of pre-bent, multifunction, bending-strain-based, bimorph transducers. Each bimorph transducer includes three pre-bent, low-K piezoelectric transducer elements configured as a piezoelectric bending-strain-based energy harvester, a pressure sensor, and a haptic device.

In each bimorph transducer, the energy harvester is disposed on the front side of a stainless-steel substrate and the pressure sensor and haptic device are disposed on the backside of the substrate. The bimorph transducer is configured such that it has a non-planar quiescent shape and can bend out of this quiescent shape in response to a force applied to the transducer. In some embodiments, the substrate of a transducer comprises a material other than stainless steel.

In the illustrative embodiment, the piezoelectric material of each transducer element is magnetron-sputter-deposited low-K aluminum nitride (AlN), which enables high-voltage operation using a very thin piezoelectric layer. In some embodiments, at least one transducer element of a bimorph transducer comprises a different low-K piezoelectric material (e.g., scandium-doped AlN, undoped ZnO, doped zinc oxide (ZnO), polyvinylidene fluoride (PVDF), doped PVDF, lithium niobate ($LiNbO_3$), etc.). In some embodiments, the piezoelectric material is deposited by a suitable technique other than magnetron sputtering, such as non-magnetron sputtering, plasma-deposition technique, and the like.

In some embodiments, the piezoelectric material of at least one transducer element is a high-K material, such as Sol-gel lead-zirconate-titanate (PZT), thick doped Sol-gel PZT, and the like.

In some embodiments, a transducer is a monomorph that includes one or more transducer elements on only the top or bottom of a substrate.

In some embodiments, a transducer includes a substrate that comprises flanges at its ends, where the flanges are thicker than the thickness of the substrate outside of the flange region. The flanges are configured such that their larger surface area compresses a greater amount of resilient material surrounding the transducer when the transducer is flattened by an applied force. The compression of the resilient material develops a potential energy that gives rise to a restoring force on the transducer once the applied force is removed.

In some embodiments, the total operational thickness of a transducer in its quiescent state is within the range of approximately 1.5 mm to approximately 9 mm. In some embodiments, the total operational thickness of a transducer is less than or equal to 3.5 mm. In some embodiments, the total operational thickness of a transducer is within the range of 1.5 to 2.0 mm.

In some embodiments, a wearable includes one or more sensors that are external to the bimorph transducers, such as a pulse-oximetry sensor, an accelerometer, a gyroscopic sensor, a temperature sensor, a force, load, one or more pressure sensors, a haptic device, and the like.

An embodiment in accordance with the present disclosure is an apparatus comprising: a bending-strain-based transducer that includes: (i) a first transducer element disposed on a first surface of a substrate, the first transducer element being a non-resonant energy harvester; and (ii) a second transducer element disposed on a second surface of the substrate, the first and second surfaces being on opposite sides of the substrate, wherein the second transducer element is selected from the group consisting of a resonant energy harvester, a non-resonant energy harvester, a force sensor, a load sensor, a pressure sensor, and a haptic device; wherein the transducer has a quiescent shape that is non-planar.

Another embodiment in accordance with the present disclosure is an apparatus comprising a first bimorph transducer having a quiescent shape that is non-planar, wherein the first bimorph transducer includes a first transducer element disposed on a first surface of a substrate, the first transducer element being a non-resonant energy harvester, and wherein the first bimorph transducer is configured to bend in response to a first force.

Yet another embodiment in accordance with the present disclosure is a method comprising forming a first bending-strain-based transducer by operations that include: forming a first transducer element on a first surface of a substrate, the first transducer element including a first piezoelectric layer, wherein the first transducer element is configured as a non-resonant energy harvester; forming a second transducer element on a second surface of the substrate, the second transducer element including a first portion of a second piezoelectric layer and being selected from the group consisting of a non-resonant energy harvester, a sensor, and a haptic device; and providing the first bending-strain-based transducer with a quiescent shape that is non-planar.

Yet another embodiment in accordance with the present disclosure comprises systems and methods for providing a graphical user interface (GUI) on a computing device (e.g., a smartphone, a tablet, a laptop computer, a desktop computer, etc.) through which a user can interact with one or more wearable devices (e.g., embodiments of wearable devices described in this application; smart watches such as Apple Watch® or Google Pixel Watch®; fitness trackers such as Fitbit® or Amazon Halo View®; etc.).

BRIEF DESCRIPTION OF THE DRAWINGS

FIGS. 3A-C depict schematic drawings of top, bottom, and cross-sectional views, respectively, of a representative transducer 104 in accordance with the illustrative embodiment.

DETAILED DESCRIPTION

Figure 1:
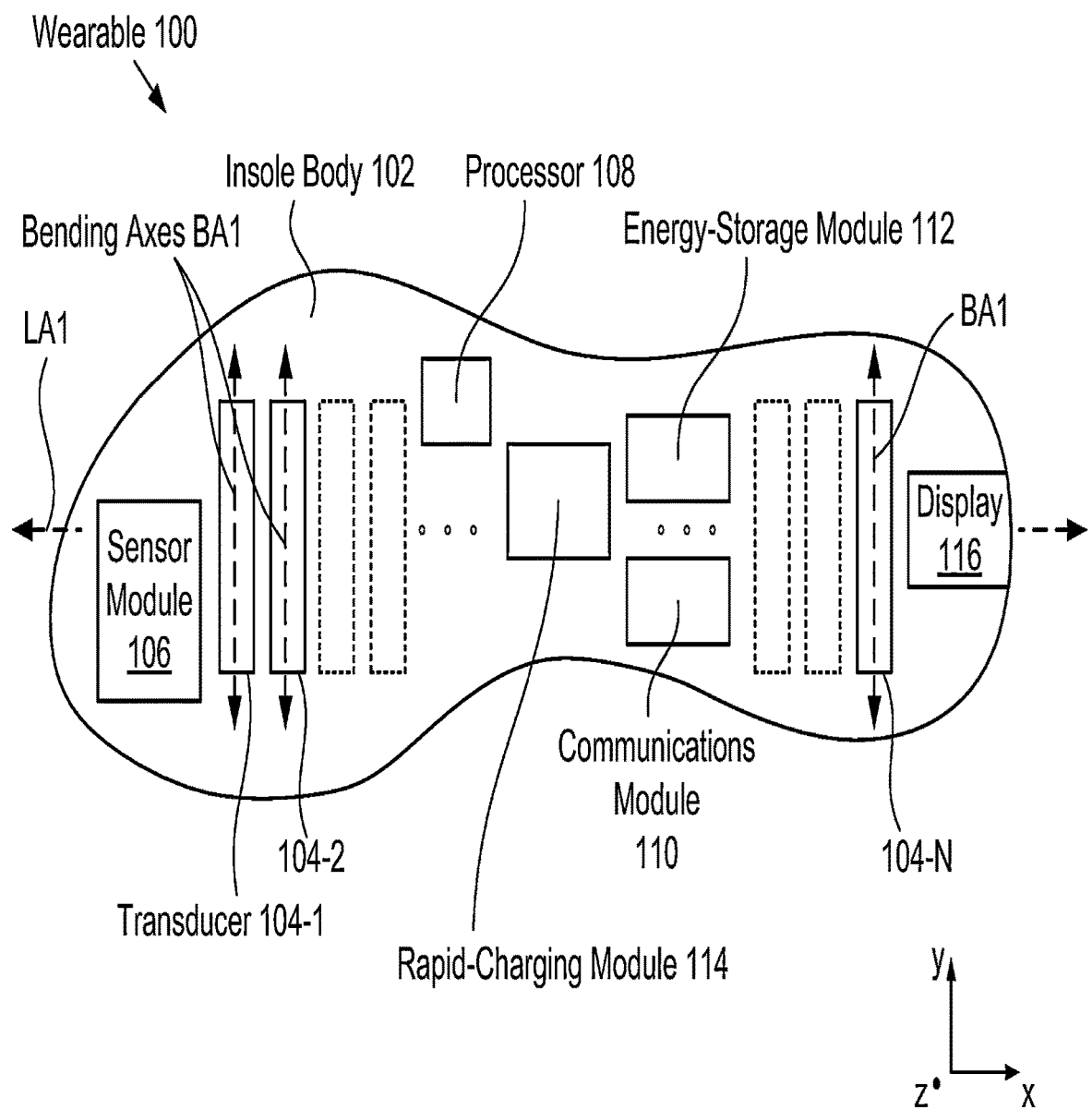
FIG. 1 depicts a schematic drawing of a plan view of an illustrative embodiment of a wearable in accordance with present disclosure.

The following merely illustrates the principles of the disclosure. It will thus be appreciated that those skilled in the art will be able to devise various arrangements which, although not explicitly described or shown herein, embody the principles of the disclosure and are included within its spirit and scope.

Furthermore, all examples and conditional language recited herein are principally intended expressly to be only for pedagogical purposes to aid the reader in understanding the principles of the disclosure and the concepts contributed by the inventor(s) to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Thus, for example, it will be appreciated by those skilled in the art that any block diagrams herein represent conceptual views of illustrative circuitry embodying the principles of the disclosure. Similarly, it will be appreciated that any flow charts, flow diagrams, state transition diagrams, pseudo code, and the like represent various processes which may be substantially represented in computer readable medium and so executed by a computer or processor, whether or not such computer or processor is explicitly shown.

The functions of the various elements shown in the Drawing, including any functional blocks that may be labeled as "processors", may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, network processor, application specific integrated circuit (ASIC), field programmable gate array (FPGA), read-only memory (ROM) for storing software, random access memory (RAM), and non-volatile storage. Other hardware, conventional and/or custom, may also be included.

Software modules, or simply modules which are implied to be software, may be represented herein as any combination of flowchart elements or other elements indicating performance of process steps and/or textual description. Such modules may be executed by hardware that is expressly or implicitly shown.

Unless otherwise explicitly specified herein, the figures comprising the drawing are not drawn to scale.

The following terms are defined for use in this Specification, including the appended claims:

"sole member" is defined as a portion of shoe sole and, as used herein, can mean at least one of a shoe insole, a shoe midsole, and a shoe outsole.

"wearable" is defined as an object meant to be worn, used, and/or carried by a user where the object includes at least one transducer, such as a sensor, haptic device, etc., and where the user can be a human or an animal. A wearable, as used herein, includes garments, undergarments (e.g., bras, shoe soles, etc.), shoes, fashion electronics (e.g., fitness trackers, smart watches, etc.), accessories (e.g., backpacks, cell phone cases, purses, wallets, etc.), sporting equipment (e.g., fitness bands, etc.), horseshoes, leashes, tethers, collars, and the like.

"bending-strain-based transducer" is defined as a transducer that is configured to bend about a bending axis located in a plane in response to a force applied at least partially along a direction normal to that plane. For example, a normally flat bending-strain-based transducer lies in a first plane when in its quiescent state but will bend out of the first plane in response to the force, while a normally curved bending-strain-based transducer will become flatter, or completely flat, in response to the force. Bending of a bending-strain-based transducer in accordance with the present disclosure can manifest as an induced curvature that is substantially uniform across at least one lateral dimension of the device or as a localized bend that occurs at one or more localized points of the device, such as at a point of support for a cantilevered or doubly-supported element.

"non-resonant energy harvester" is defined as an energy harvester that does not require a driving force at or near its natural resonant frequency to generate voltage and/or electrical power. For example, a non-resonant energy harvester can generate voltage and/or electrical power in response to an aperiodic stimulus or the application of a substantially constant force.

"aligned" is defined as being co-linear or parallel with. For example, two elements that are aligned can either be arranged along the same axis or arranged such that they are parallel with one another.

"low-K piezoelectric material" is defined as a piezoelectric material having a dielectric constant that is less than or equal to 30 at room temperature.

"high-K piezoelectric material" is defined as a piezoelectric material having a dielectric constant that is greater than or equal to 100 at room temperature.

FIG. 1 depicts a schematic drawing of a plan view of an illustrative embodiment of a wearable in accordance with present disclosure. Wearable 100 is an orthotic shoe insole that can be reversibly inserted into a shoe. In the depicted example, wearable 100 comprises insole body 102, transducers 104-1 through 104-N, sensor module 106, processor 108, energy-storage module 110, communications module 112, rapid-charging module 114, and display 116.

It should be noted that, although the illustrative embodiment comprises a wearable that is a shoe insole, the teachings of the present disclosure can be applied to virtually any wearable suitable for use by a human, an animal, a robot, or as part of an exoskeleton. Furthermore, the teachings of the present disclosure, when applied to footwear (e.g., shoes, sneakers, cleats, slippers, socks, etc.), are not limited to reversibly insertable insoles but, rather, can be applied to myriad sole members, such as shoe insoles that are permanently joined to a shoe, outsoles, mid-soles (e.g., for high heel shoes, etc.), or to footwear that is, itself, a wearable comprising removable or non-removable non-resonant energy harvesters, sensors, and the like.

Figure 2:
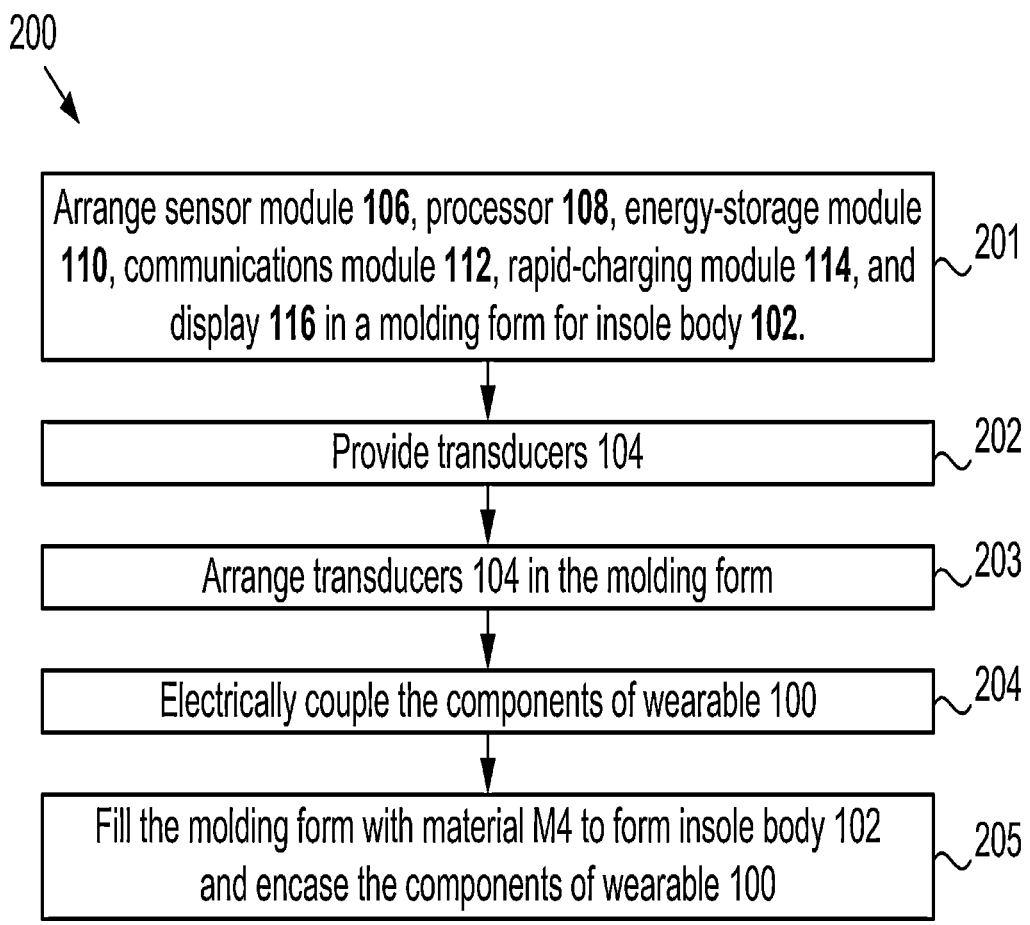
FIG. 2 depicts operations of a method for forming a wearable in accordance with present disclosure.

FIG. 2 depicts operations of a method for forming a wearable in accordance with present disclosure. Method 200 begins with operation 201, wherein sensor module 106, processor 108, energy-storage module 110, communications module 112, rapid-charging module 114, and an optional display 116 are arranged in a molding form suitable for the formation of insole body 102.

Insole body 102 is a conventional shoe insole comprising a resilient material suitable for providing cushioning to the user. Insole body 102 is a substantially "foot-shaped" body comprising material M1. Insole body 102 is characterized by longitudinal axis LA1, which is substantially aligned with the long dimension of the insole body (i.e., from the heel to the toes of the user, or vice versa).

Each of transducers 104-1 through 104-N (referred to, collectively, as transducers 104) is a multi-function bimorph transducer that includes a non-resonant energy harvester that is configured to operate in bending mode rather than compression. In the depicted example, each of transducers 104 includes a non-resonant energy harvester, a pressure sensor, and a haptic device for providing a sensory signal to the user. A representative transducer 104 is described in more detail below and with respect to FIGS. 3A-C.

Sensor module 106 includes one or more sensors for measuring user-based and/or environmental parameters other than pressure. Examples of sensors suitable for inclusion in sensor module 106 include, without limitation, temperature sensors, chemical sensors (e.g., oxygen sensors, humidity sensors, salinity sensors, electrolyte sensors, ion sensors, etc.), volatile organic compound (VOC) sensors for measuring ambient concentrations of "reducing gases" associated with air quality—e.g. alcohols, aldehydes, ketones, organic acids, amines, organic chloramines, aliphatic and aromatic hydrocarbons (e.g. for detection of the onset of "athletes foot" or other ailments), GPS sensors, accelerometers, gyroscopes, inertial sensors, optical sensors, including but not limited to pulse-oximetry sensors, carbon dioxide sensors, blood-alcohol sensors, glucose sensors, infrared (IR) temperature sensors, and the like.

In the depicted example, sensor module 106 includes a GPS system, a pulse-oximetry sensor, and a multi-axis accelerometer. The GPS system provides location and elevation information to processor 108 and transmits and receives information to/from communications module 110.

The pulse-oximetry sensor provides user-centric data to processor 108, such as heart rate and blood oxygen level. Respiratory rate and burned calories can be calculated from heart rate. It is known that the respiratory rate calculation is accurate, yet the burned calories of contemporary wearable smart watches using this conversion technique are known to be inaccurate.

The multi-axis accelerometer enables wearable 100 to detect walking, running, skipping, etc., as well as calculation of burned calories by the human or animal body with an accuracy that greater exceeds the accuracy possible in the prior art. The aforementioned heart rate calculation method is used in combination with the multi-axis accelerometer to obtain these superior results via a computer software algorithm.

It is an aspect of the present disclosure that calorie burning can be determined with higher accuracy than possible in the prior art because transducer 100 enables measurement of the actual mechanical power expended, where P=(force F=mass m*acceleration $a_{x,\ y\ or\ z}$)*(speed S=$a_{x,\ y\ or\ z}$*time t), which can then be converted to human power (or animal power) using a known conversion factor to determine calories burned with less than 5% inaccuracy. Prior-art systems use only the measured heart rate to calculate burned calories, which has been found to be 27% to 93% inaccurate.

The multi-axis accelerometer also enables wearable 100 to detect potentially catastrophic events, such as a fall by the user, as well as assess user behavior, such as after a fall has been detected. For example, the accelerometer enables detection of a lack of movement (potentially indicating a state of unconscious), rapid, random movements (potentially indicating onset of a seizure), movements indicative of crawling (e.g., to call for help, etc.), as well as other user-centric behavior, such as when the user is lying down, etc.

In some embodiments, a second, external multi-axis accelerometer (e.g., located in a wrist band, a chest band, a garment, a smart watch, a fitness tracker, etc.) is used in conjunction with wearable 100 to provide additional information regarding upper body movements. Such an arrangement enables better determination of the calories burned by the upper body, providing improved accuracy for overall calorie-burn calculations.

In some embodiments, the location of the pulse-oximetry sensor, IR temperature sensor or other optical sensor within wearable 100 is carefully selected relative to advantageously position it relative to the blood vessels (e.g., arteries carrying oxygen-laden red blood cells) in the body portion of the user with which it is to be operatively coupled.

Processor 108 includes processing circuitry, control circuitry, memory, and the like, that is configured to, among other things, send and receive signals to/from transducers 104 and sensor module 106, execute instructions, analyze and store data, and transmit and receive signals to/from communications module 112. In the depicted example, the processor is implemented as a single, discrete component within wearable 100; however, in other embodiments, the processor can be distributed, at least in part, among multiple components in wearable 100, implemented, in part or in full, in a remote or cloud-based computing system, or otherwise implemented in a suitable arrangement for carrying out the functions described herein. In some embodiments, some or all of the capability of processor 108 is incorporated into communications module 110.

Communications module 110 is configured to enable wireless communications to and from wearable 100. In some embodiments, communications module 110 employs one or more communications systems, such as Bluetooth® low-energy (BLE) communications system, LoRa, long-range cellular, satellite, Bluetooth®, WiFi, Zigbee, A-wave, radio frequency (RF), and the like. In the depicted example, communications module 110 includes a LoRa communications system and a Bluetooth® low-energy (BLE) communications system. The LoRa communications system is configured to transmit and receive GPS data to/from wearable 100 via cellular communications networks, while the BLE system is configured to communicate with processor 108 and other components within wearable 100. In the depicted example, the BLE system is also configured to communicate with a base station, such as a dedicated base station or a mobile device running a dedicated app for interfacing to wearable 100.

It should be noted that the relatively larger amount of space available in an insole than, for example, in a mobile phone, enables the communications antennae of communications module 110 to be designed to enable better reception and more consistent transmission to/from their respective paired devices.

It is an aspect of the present disclosure that the inclusion of a GPS system in sensor module 106 and a communications module that communicates with a mobile device, such as a cell phone, tablet, etc., enables high-level functionality, such as computer applications that enable location of a wearable at any time, or an alarm when a distance between the wearable and base station or mobile device exceeds a threshold. This is particularly useful for locating a user that might require assistance (e.g., a missing child, a "wandering" lost Alzheimer's patient, an intoxicated user, a missing camper/hiker/skier, a lost animal, a missing robot, etc.).

Energy-storage module 112 includes power-handling circuitry (e.g., AC to DC rectification, etc.) and one or more energy storage units. Energy-storage module 112 is operatively coupled with each of transducers 104 and configured to store energy generated by their respective non-resonant energy harvesters, as well as provide power to the transducers and the other electronics included in wearable 100. In the depicted example, energy-storage module 112 includes a lithium-polymer battery suitable for storing enough charge for several hours/days of normal use. In some embodiments, energy-storage module 112 includes one or more super capacitors and/or a different energy-storage device, such as a rechargeable battery, a rechargeable standard capacitor, a hybrid-system of a primary battery and/or a rechargeable battery and/or a super capacitor and/or a capacitor, and the like.

Rapid-charging module 114 is optionally included in wearable 100 and includes an interface for electrically coupling to an external power source to rapidly charge the energy storage units of energy-storage module 112. In the depicted example, rapid-charging module 114 includes an inductive-charging coil sub-system and associated circuitry. In some embodiments, the rapid-charging module includes a different interface that enables electrical connection to an external power source.

Display 116 is optionally included in wearable 100 to enable visual determination of the state of the wearable, such as charge level, etc. In the depicted example, display 116 includes a plurality of LEDs; however, other display elements can be used in display 116 without departing from the scope of the present disclosure.

At operation 202, transducers 104 are provided.

FIGS. 3A-B depict schematic drawings of simplified top and bottom views, respectively, of a representative transducer 104 in accordance with the illustrative embodiment.

Figure 3C:
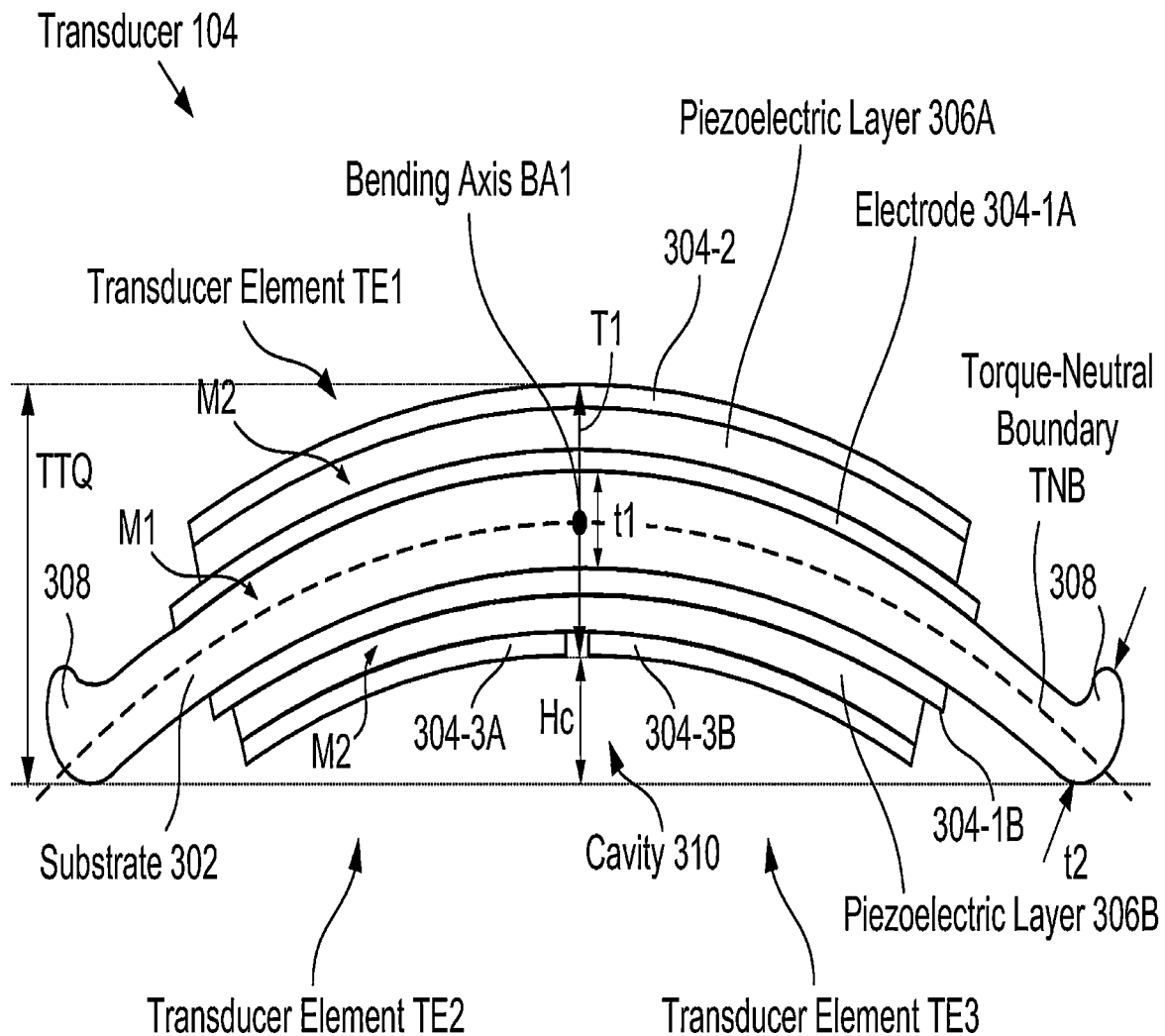

FIG. 3C depicts a schematic drawing of a detailed sectional view of the layer structure of transducer 104 in accordance with the illustrative embodiment. The sectional view shown in FIG. 3C is taken through line a-a, as indicated in FIG. 3A.

Transducer 104 includes substrate 302 and transducer elements TE1, TE2, and TE3. Transducer element TE1 is disposed on the top surface of substrate 302, and transducer elements TE2 and TE3 are disposed on the bottom surface of substrate 302, collectively forming a bimorph-transducer structure. Because the physical configuration of transducer element TE1 is substantially equivalent to that of the combination of transducer element TE2 and TE3, the structure is balanced about substrate 302 and transducer 104 is characterized by torque-neutral boundary TNB, which runs through the center of the substrate.

Transducer 104 is configured as a "ridge transducer" having a non-planar quiescent shape that curved along one dimension (the x-dimension in the depicted example), thereby forming a ridge along an orthogonal dimension (i.e., the y-dimension), as well as a cavity beneath the ridge. The ridge of transducer 104 is substantially aligned with bending axis BA. In some embodiments, transducer 104 has a cross-section along at least one dimension that is described by a known curved shape, such as sinusoidal, parabolic, catenary, and the like.

It is an aspect of the present disclosure that a piezoelectric transducer having a quiescent shape that is non-planar affords significant advantages over prior-art piezoelectric transducers, such as:
- improved reliability due to inherent overstress limit; or
- increased restoring force; or
- increased energy generation for a given force; or
- any combination of i, ii, and iii.

Although the illustrative embodiment includes rectangular piezoelectric transducers, in some embodiments, at least one piezoelectric transducer in a wearable has a non-rectangular shape. In some embodiments the non-rectangular shape (e.g. circular) piezoelectric transducers may be used as a force sensor (e.g. step-counter) or as a haptic device or both.

In some embodiments, transducer is configured as a concave (or convex disc) that is radially symmetric about its center point that defines a peak (or center of a valley).

In some embodiments, transducer 104 is a ruffled transducer having a series of ridges and furrows aligned with one dimension. In some embodiments, transducer 104 is shaped such that it is ruffled in two dimensions (i.e., has peaks and valleys along two dimensions (e.g., the x- and y-dimensions), thereby defining a "waffle-like" structure. In some such embodiments, the shape of transducer is defined such that strain is distributed substantially evenly along at least one dimension.

Transducer element TE1 is configured as a non-resonant energy harvester and includes electrodes 304-1A and 304-2 and piezoelectric layer 306A. Transducer element TE1 is configured to generate electrical energy in response to deformation of piezoelectric layer 306A out of its quiescent shape due to an applied force.

Transducer element TE2 is configured as a pressure sensor and includes electrodes 304-1B, 304-3A, and a first portion of piezoelectric layer 306B. Transducer element TE2 is configured to provide an electrical signal whose magnitude is based on the amount of strain induced in the region of piezoelectric layer 306B between electrodes 304-1B and 304-3A by the bending of substrate 302 in response to the applied force. As a result, the electrical signal provided by transducer element TE2 is indicative of the magnitude of applied force F.

Transducer element TE3 is configured as a haptic device and includes electrodes 304-1B, 304-3B, and a second portion of piezoelectric layer 306B. Transducer element TE3 is configured to generate a vibration signal that is perceptible to the user of wearable 100 in response to a drive signal provided by processor 108. As a result, transducer 100 can provide signals to the user in the case of potential foot slippage, a potential mis-step, detected body-balance issues, as part of behavioral retraining during, for example, physical therapy after a stroke, a wake-up alarm, and the like. In some embodiments, haptic devices are arranged around the perimeter of the foot to enable their use as directional stimuli for helping vision-impaired persons safely navigate through a landscape. In some embodiments, the haptic devices are operatively coupled with a voice-controlled handheld mobile device, or alarm to, for example, provide an audible warning if the user is about to walk into a street intersection with automobiles passing or across train tracks, and the like.

Although the illustrative embodiment includes a multi-function transducer having energy harvesting, sensing, and haptic feedback capabilities, in some embodiments, transducer 104 includes only non-resonant energy harvesters, only a non-resonant energy harvester and a sensor, or only a non-resonant energy harvester and a haptic device.

Figure 4:
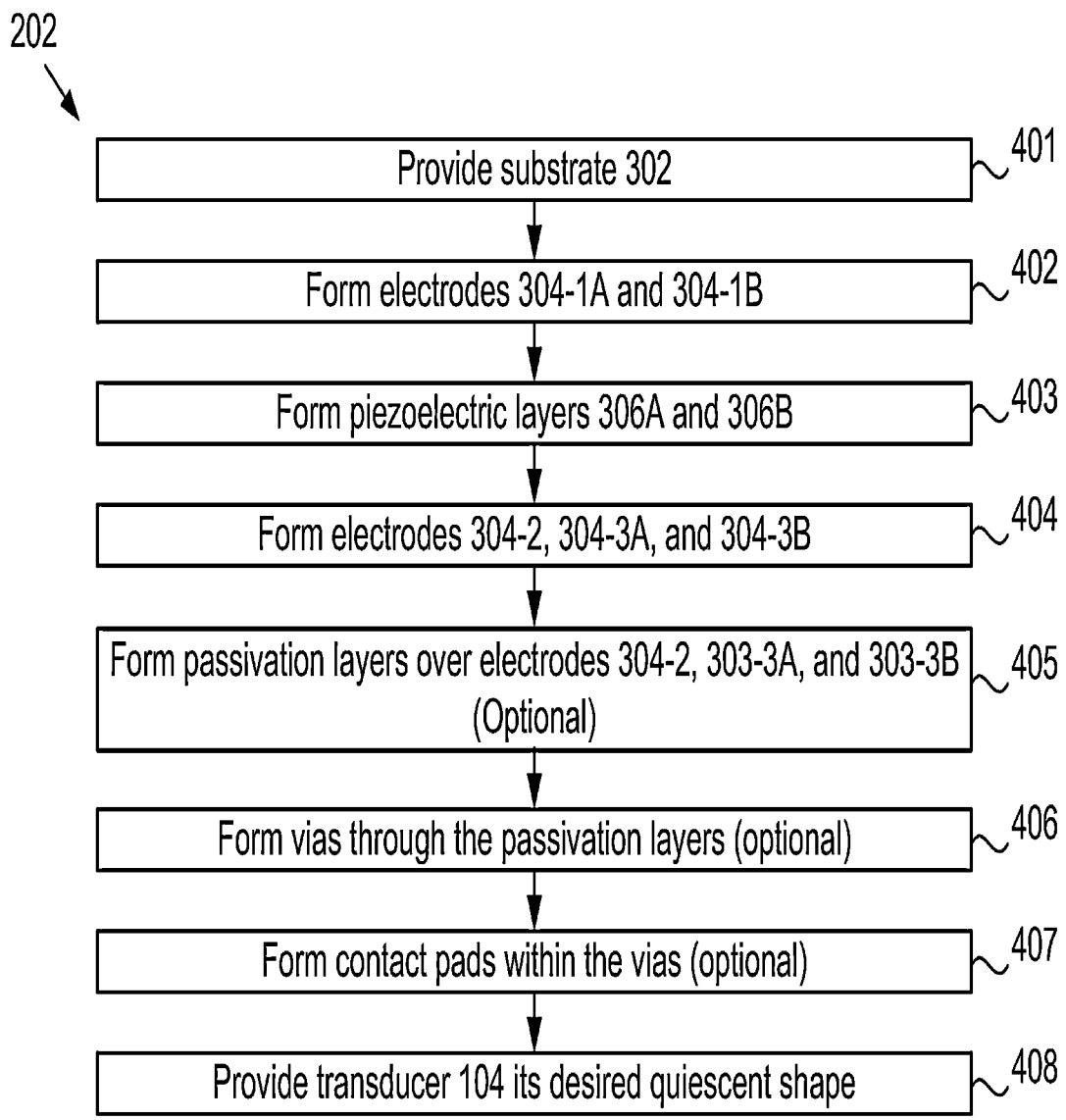
FIG. 4 depicts sub-operations suitable for forming a transducer in accordance with the present disclosure.

FIG. 4 depicts sub-operations suitable for forming a transducer in accordance with the present disclosure. Operation 202 begins with sub-operation 401, wherein substrate 302 is provided.

Substrate 302 is a flexible substrate suitable for planar processing methods. Substrate 302 comprises a layer of material M1 having thickness, t1.

Material M1 is selected to provide a desired combination of flexibility, yield strength, and plastic-deformation point. As discussed below, in order to form a pre-bent transducer, such as transducer 104, the plastic-deformation point of material M1 must be less than or equal to the yield strength of the material included in piezoelectric layers 306A and 306B. As a result, the piezoelectric layers deposited on the substrate will not fracture when the substrate is deformed from its initial planar configuration into its quiescent non-planar shape. It is an aspect of the present disclosure that a transducer whose substrate has a plastic deformation point that is within the range of approximately 70% to approximately 80% of the fracture stress point of its piezoelectric material affords particular advantages over the prior art.

The thickness, t1, of substrate 302 depends on the choice of material M1 and is typically within the range of approximately 10 microns to approximately 1.5 mm; however, a thickness within the range of approximately 200 microns to approximately 750 microns is preferable for many applications.

In the depicted example, material M1 is sintered stainless steel having a Young's modulus ($E_y$) of approximately 190 MPa and a plastic-deformation point of approximately 1400 MPa. It should be noted that sintered stainless steel can have a plastic-deformation point of up to 1500 MPa depending on sintering temperature and time. As a result, in some embodiments, M1 has a different plastic-deformation point that is less than or equal to 1500 MPa.

The choice of stainless steel and, in particular, sintered stainless steel as material M1 enables the thickness of substrate 302 to be very thin compared to most alternative materials. The minimum value for t1 is dictated by a need for substrate 302 to generate sufficient restoring force when deformed to enable it to return fully to its quiescent state once the applied force is removed. The maximum value of t1 is dictated by a need to enable the substrate to deform fully in response to a reasonable amount of applied force. For a transducer that is intended for use in an insole and whose substrate comprises sintered stainless steel, for example, a suitable value for t1 is typically within the range of 500 microns to approximately 1.5 mm. In the depicted example, t1 is equal to 600 microns.

In some embodiments, M1 comprises a different material and/or substrate 302 has a different thickness, t1. Materials suitable for use in substrate 302 include, without limitation, low-Young's modulus materials (e.g., polyimides, polydimethylsiloxane (PDMS), plastics, etc.), moderate-Young's modulus materials (e.g., flexible glasses, Corning Willow® glass, etc.), and high-Young's modulus materials (e.g., metals (e.g., brass, copper, etc.), composite materials, and the like). It should be noted that the use of a different substrate material will not change the output voltage/power/energy of a symmetric bimorph transducer having the same design in every other respect, since the torque-neutral axis or boundary TNB and resulting strain of the piezoelectric layers remain unchanged.

It should be noted that the use of a metal, such as stainless steel, sintered stainless steel, brass, copper, etc., for substrate 302 affords embodiments in accordance with the present disclosure significant advantages over the prior art, including an ability to match the yield strengths of the substrate material and that of the piezoelectric layers, low cost, well-known production methods, and most metals can be sawed, diced, laser cut, water-jet cut, etc. without requiring exotic methods. Furthermore, most metals suitable for use in substrate 302 are available in sheets suitable for use in large production environments, such as large area flat panel or roll-to-roll manufacture.

At optional sub-operation 402, electrodes 304-1A and 304-1B are formed on the top and bottom surfaces, respectively of substrate 302.

Although not shown in FIG. 3C (for clarity), adhesion layers are typically deposited on the top and bottom surfaces of substrate 302 prior to the formation of electrodes 304-1A and 304-1B. Such adhesion layers normally have a thickness of less than 1000 nm and typically are 100 nm or less and comprise the same material as that of piezoelectric layers. In some embodiments, these adhesion layers comprise an alternate metal, such as titanium or molybdenum, as discussed in detail in parent application U.S. patent application Ser. No. 17/373,690. Using titanium (Ti), molybdenum (Mo) or other conduction material as the adhesion layer allows for electrical connection from lower electrodes 304-1A and 304-1B to the metal substrate 302, which may be more manufacturable to electrically connect to by external wiring post fabrication.

Electrodes 304-1A and 304-1B are layers of conductive material suitable for providing electrical connectivity to piezoelectric layers 306A and 306B, respectively. In the depicted example, each of electrodes 304-1A and 304-1B is a layer of sputter-deposited molybdenum (Mo) having a thickness of approximately 2 microns. Preferably, each electrode has a thickness within the range of approximately 100 nm to approximately 2 microns.

It should be noted that the material and thickness used for the electrodes is a matter of design choice and is affected by the choice of material M2 used for piezoelectric layers 306A and 306B. For example, sputtered PZT is preferably deposited on copper or copper alloys (e.g. brass). In each of these cases (AlN or PZT), the aforementioned electrode metals yield the best polycrystalline orientation, which yields the best piezoelectric coefficients $d_{ij}$ (i or j=1, 2 or 3 or equivalently x, y or z), voltage and power/energy output. Yet, provided adequate adhesion can be realized, any metal can be used for the electrodes.

At sub-operation 403, piezoelectric layers 306A and 306B are formed on electrodes 304-1A and 304-1B, respectively.

Each of piezoelectric layers 306A and 306B is a layer of piezoelectric material M2 having a yield strength that exceeds the plastic-deformation point of substrate 302. Typically, each of piezoelectric layers 306A and 306B has a thickness that is within the range of approximately 0.1 microns to approximately 10 microns; however, thicknesses of up to several hundred microns can be used for at least one of piezoelectric layers without departing from the scope of the present disclosure. It is preferable that both piezoelectric layers 306A and 306B are equal in thickness so that the torque neutral boundary (or axis) is located at the center of the substrate 302. Such a configuration yields substantially optimal output voltage and power/energy generation. Preferably, material M2 is a low-K piezoelectric material.

In the depicted example, piezoelectric layers 306A and 306B are sputter-deposited layers of undoped aluminum nitride (AlN) having a thickness of approximately one micron. Preferably, the thickness of undoped aluminum nitride used in piezoelectric layers 306A and 306B is within the range of approximately 0.1 to approximately 4.0 microns (provided adhesion of such layers is sufficient to ensure long-term reliability).

In some embodiments, piezoelectric layers 306A and 306B comprise sputtered scandium-doped aluminum nitride (ScAlN), which can have a Young's modulus that is reduced by as much as 20% from that of undoped AlN by up to 20%, making it more flexible. As a result, ScAlN is particularly attractive for use as material M2 in some embodiments because it gives rise to larger piezoelectric coefficients $d_{ij}$ (up to 2.5×) for the same deformation as compared to undoped AlN.

Furthermore, as will be apparent to one skilled in the art, after reading this Specification, to first order, the voltage, V, generated by a piezoelectric layer is proportional to $(d_{31}/K)$ and the power, P, generated is proportional to $(d_{31}^2/K)$. Since output voltage is proportional to $d_{ij}$ and $E_y$, and output power is proportional to $d_{ij}^2$ and $E^2$, increased energy harvesting can be achieved using the same thickness piezoelectric layers, thereby enabling more voltage/power/energy generation and more flexibility and/or low-profile effectively thinner transducers. However, the introduction of scandium (and associated defects) into AlN can also reduce the fracture point of material M2 below the plastic deformation point of material M1, which would reduce the maximum curvature that could be imparted on transducer 106.

The use of undoped aluminum nitride or scandium-doped aluminum nitride in piezoelectric layers 306A and 306B affords embodiments in accordance with the present disclosure significant advantages over transducers and wearables known in the prior art, including:

higher voltage and power/energy generation capability; or
higher yield strength; or
significantly lower bending profile; or
increased flexibility; or
differentially matched yield strength with a steel substrate allowing for fabricating pre-bent structures post AlN or ScAlN deposition; or
environmental friendliness (no lead content, as opposed to PZT); or
any combination of i, ii, iii, iv, v, and vi.

It should be noted that, although undoped aluminum nitride or scandium-doped aluminum nitride is preferred for material M2, other piezoelectric materials can be used for at least one of piezoelectric layers 306A and 306B without departing from the scope of the present disclosure. Materials suitable for use in accordance with the present disclosure include, without limitation, thin, magnetron sputtered, low-K piezoelectric materials (e.g., undoped zinc oxide (ZnO), doped ZnO, undoped polyvinylidene fluoride (PVDF), doped PVDF, chromium-doped AlN, yttrium-doped AlN, lithium niobate ($LiNbO_3$), etc.), thick high-K piezoelectric materials (e.g., undoped Sol-gel lead zirconate titanate (PZT), doped Sol-gel PZT, etc.), and the like.

Dopants suitable for inclusion in piezoelectric layers 306A and/or 306B include, without limitation, strontium, lanthanum, iron, barium, niobium, europium, cerium oxide, lithium aluminum, sodium, potassium, boron, graphene, trifluoro ethylene, zinc oxide, nitrogen, magnesium, magnesium oxide, scandium, chromium, yttrium, silver, tin, and lithium, as well as combinations thereof.

Although it is preferable that material M2 is a low-K piezoelectric material, material M2 can comprise a high-K piezoelectric material without departing from the scope of the present disclosure. For example, in some embodiments, one or both of piezoelectric layers 306A and 306B comprises a very thick (e.g. 25 to 250 or more microns) layer of Sol-gel lead-zirconate-titanate (PZT) or doped Sol-gel PZT. Such a layer can be formed, for example, by spin coating, extrusion, lamination, etc. The significantly greater thickness of such a layer can compensate for the high dielectric constant of these materials (PZT has a K in the range of 1700-3500, for instance), which would normally lead to low voltage and poor power generation.

Furthermore, deposition methods other than sputter deposition can be used to form one or both of piezoelectric layers 306A and 306B without departing from the scope of the present disclosure. Alternative deposition methods suitable for forming piezoelectric layers 306A and 306B include, without limitation, Sol-gel coating, chemical-vapor deposition (CVD), plasma-enhanced chemical vapor deposition (PECVD), wet-chemical processing, doctor-blade deposition, spin coating, and the like.

At sub-operation 404, electrode 304-2 is formed on piezoelectric layer 306A and electrodes 304-3A and 304-3B are formed on piezoelectric layer 306B. Electrodes 304-2, 304-3A, and 304-3B are analogous to electrodes 304-1A and 304-1B described above.

As will be apparent to one skilled in the art, the dimensions of electrodes 304-2, 304-3A, and 304-3B define the sizes of transducer elements TE1, TE2, and TE3, respectively. As a result, transducer element TE1 has width W1 and length L1, transducer element TE2 has width W2 and length L2, and transducer element TE3 has width W3 and length L2. As will be apparent to one skilled in the art, the values of L1, L2, W1, W2, and W3 depend upon the application for which transducer 104 is intended. In the depicted example, wearable 104 is an insole configured to fit within a women's shoe, which normally has an approximately 7-cm width. As a result, each of L1 and L2 is 6 cm, width W1 is 3 cm, and widths W2 and W3 are 2.75 cm. In some embodiments, wearable 100 is an insole configured for insertion into a men's shoe, which has an approximately 9-cm width, enabling transducer lengths of approximately 8 cm.

In some embodiments, electrode 304-2 comprises two discontinuous electrode portions that are separated by a small gap such that they are electrically disconnected. In some such embodiments, an electrically conductive jumper is formed to electrically connect the two electrode portions. When electrically connected via a jumper, the two electrode portions substantially function as one complete electrode on the top of piezoelectric layer 306A.

At optional sub-operation 405, passivation layers (e.g., silicon oxide, silicon nitride, polyimide, etc.) are formed over electrodes 304-1A, 304-1B, 304-2, 304-3A, and 304-3B. Typically, the passivation layers have a thickness within the range of approximately 0.5 micron to approximately 3 microns. In the depicted example, the passivation layers are PECVD-deposited silicon nitride having thickness of approximately 1 micron.

At optional sub-operation 406, vias are formed through the passivation layers to enable access to each of at least one of electrodes 304-1A, 304-1B, 304-2, 304-3A, and 304-3B.

At optional sub-operation 407, contact pads are formed in the vias to enable electrical connections to be made to at least one of electrodes 304-1A, 304-1B, 304-2, 304-3A, and 304-3B.

As noted above, the use of certain low-K piezoelectric materials (e.g., undoped aluminum nitride or scandium-doped aluminum nitride, etc.) enables a very thin transducer to generate more voltage/power/energy. It is an aspect of the present disclosure that the transducer thickness, T1, of transducer 104 (as depicted in FIG. 3C) can be kept within the range of approximately 10 microns to approximately 1.6 mm, while still generating sufficient output for many applications. As a result, embodiments in accordance with the present disclosure are better suited than prior-art transducers for some wearable applications, such as shoe-sole elements, bras, etc., where a transducer thicker than a few millimeters would be noticeable and could even cause discomfort. In the depicted example, the transducer thickness, T1, of transducer 104 is approximately 612 microns.

At sub-operation 408, transducer 104 is provided its quiescent non-planar shape.

In the depicted example, transducer 104 is formed into a "u-shaped" channel having flanged edges by heating it above the glass-transition point of substrate 302 and applying mechanical force to "press" the transducer into its desired quiescent shape. Once formed, transducer 104 defines underlying cavity 310.

In its quiescent state, the total transducer height TTQ of transducer 104 is equal to the sum of transducer thickness T1 and the cavity height, Hc, of cavity 310.

It is an aspect of the present disclosure that the non-planar quiescent shape into which transducer 104 can be formed is limited only by the yield strength of material M2, as long as:

the material of piezoelectric layers 306A and 306B and electrodes 304-1A, 304-1B, 304-2, 304-3A, and 304-3B have melting points that are greater than the glass-transition point of the substrate; and the plastic-deformation point of the substrate material (i.e., M1) is less than or equal to the yield strength of the material (i.e., M2) of the piezoelectric layers.

However, there are several other factors that inform the desired values for T1 and Hc, as well as the material choices for substrate 302, piezoelectric material M2, and electrodes 304. These factors are, in large part, dictated by the application for which a transducer is intended.

For example, when transducer 104 is intended for use in an insole, it is desirable that TTQ be small enough to avoid user discomfort during use, thereby placing an upper bound on transducer thickness T1 and/or cavity height Hc. At the same time, a transducer must be able to develop sufficient restoring force when deformed by force F to enable it to return to its quiescent state when the force is removed (e.g., when the user's foot lifts during walking, even if the shoe is tied very tightly). In addition, preferably, a transducer exhibits maximum deformation, without undergoing plastic deformation, in response to the applied force so that it generates as much electrical energy as possible.

As discussed below and with respect to FIGS. 6A-B, typical practical values for TTQ are within the range of approximately 1.5 mm to approximately 9.5 mm for transducers designed for use in an insole. In the depicted example, wearable 100 is an orthotic insole and TTQ is approximately 3.5 mm; however, TTQ can have any practical value without departing from the scope of the present disclosure.

Flanges 308 are located at the lower edges of substrate 302. Flanges 308 are configured such that they have more surface area to compress the material of insole body 102 when transducer 104 is deformed by an applied force. In the depicted example, flanges 308 are portions of the substrate that are "rolled" inward such that they have thickness t2, which is greater than the thickness of the rest of the substrate (i.e., M. As a result, flanges 308 As discussed in more detail below and with respect to FIGS. 6A-B, the increased surface area of flanges 308 increases the amount of material displaced along the x-direction when transducer 104 is flattened, thereby increasing the potential energy stored by the insole-body material, which is typically resilient. As a result, flanges 308 increase the magnitude of a lateral restoring force on the transducer that arises as the transducer is flattened.

In some embodiments, transducer 104 is formed into its non-planar quiescent shape via a different conventional method, such as die stamping, etc.

Returning now to method 200, in operation 203, transducers 104 are arranged in the molding form for insole body 102. In the depicted example, transducers 104 are arranged in a substantially linear arrangement in which the short axis, SA1, of each transducer is substantially aligned with longitudinal axis LA1 of insole body 102. As a result, the arrangement of transducers can "roll up" along longitudinal axis LA1 (like a venetian blind) as insole 102 deforms during a stride of the user.

Although the depicted example includes a plurality of substantially identical transducers 104 that is arranged in a linear arrangement within wearable 100, a plurality of transducers within a wearable can include different transducers and/or be arranged in any practical one-, two-, or three-dimensional arrangement without departing from the scope of the present disclosure. For example, a smart connected insole in accordance with the present disclosure can include a plurality of transducers 104 having a shorter length, or circular transducers, etc., in the narrower instep region of the insole. Some non-limiting examples of alternative transducer arrangements are disclosed in detail in parent application U.S. patent application Ser. No. 17/373,690.

At operation 204, the components within wearable 100 are electrically connected such that power is provided by the non-resonant energy harvesters of transducers 104 via energy storage module 112.

Figure 5:
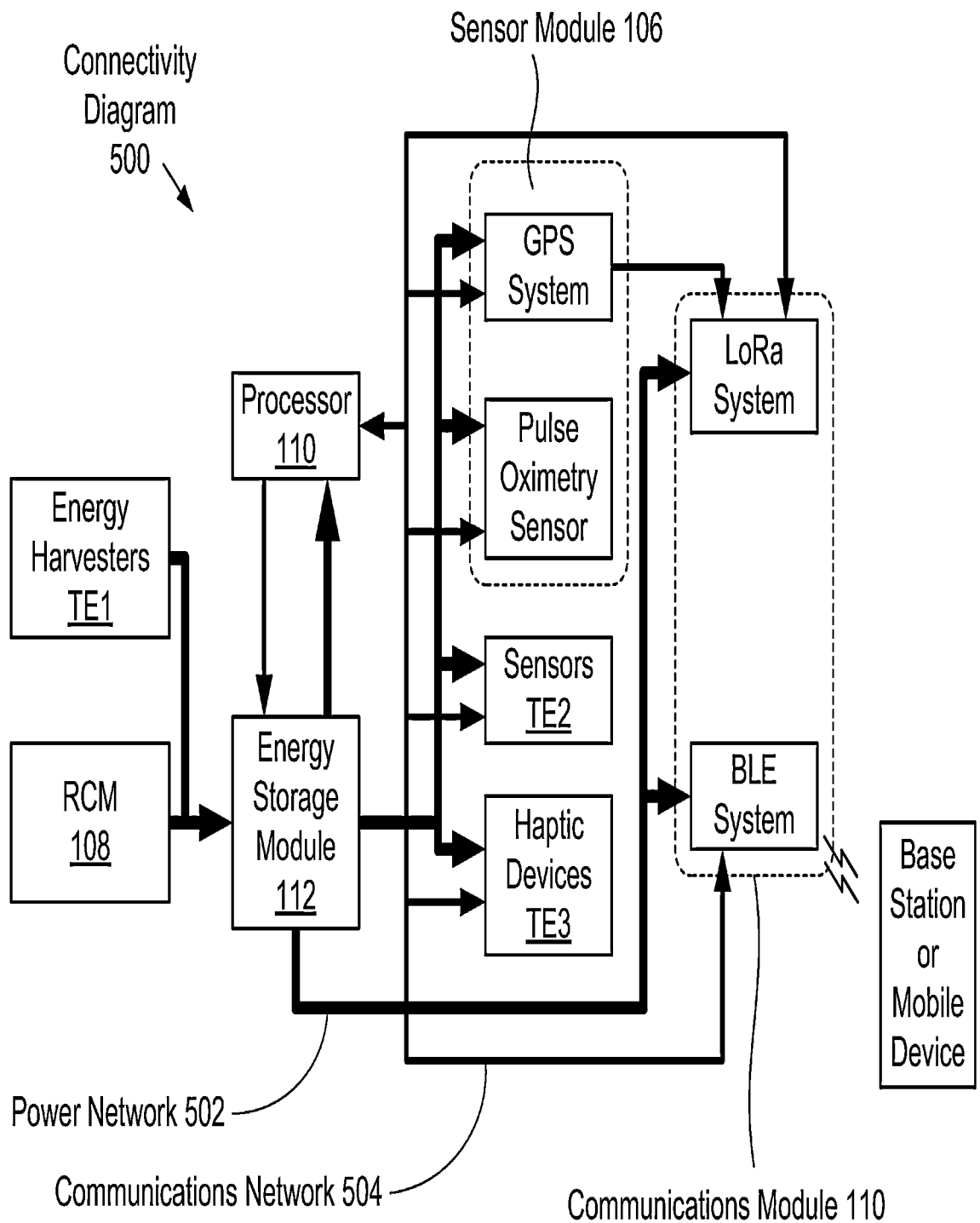
FIG. 5 depicts a block diagram showing component connectivity for a wearable in accordance with the present disclosure.

FIG. 5 depicts a block diagram showing component connectivity for a wearable in accordance with the present disclosure.

As seen in connectivity diagram 500, wearable 100 includes two substantially independent networks—power network 502 and communications network 504.

In power network 502, energy storage module 112 receives energy from each of rapid-charging module 108 and the non-resonant energy harvesters TE1 included in the plurality of transducers 104 and distributes the energy, as needed, to other components within wearable 100, including processor 108, sensor module 106, the force/load/pressure sensors TE2 included in the plurality of transducers 104, the haptic devices TE3 included in the plurality of transducers 104, and communications module 110.

In communications network 504, energy data and control signals are transmitted between processor 108 and the components in sensor module 106, communications module 110, and energy storage module 112.

At operation 205, insole body 102 is formed by filling the mold to fully encase transducers 104-1 through 104-N, sensor module 106, processor 108, communications module 110, energy-storage module 112, rapid-charging module 114, and display 116. By fully encasing these components within the insole, they are substantially protected from damage due to water, sweat, and the like. In some embodiments, display 116 is encased within insole body 102 such that its display elements are visible to the user when desired.

Figure 6A:
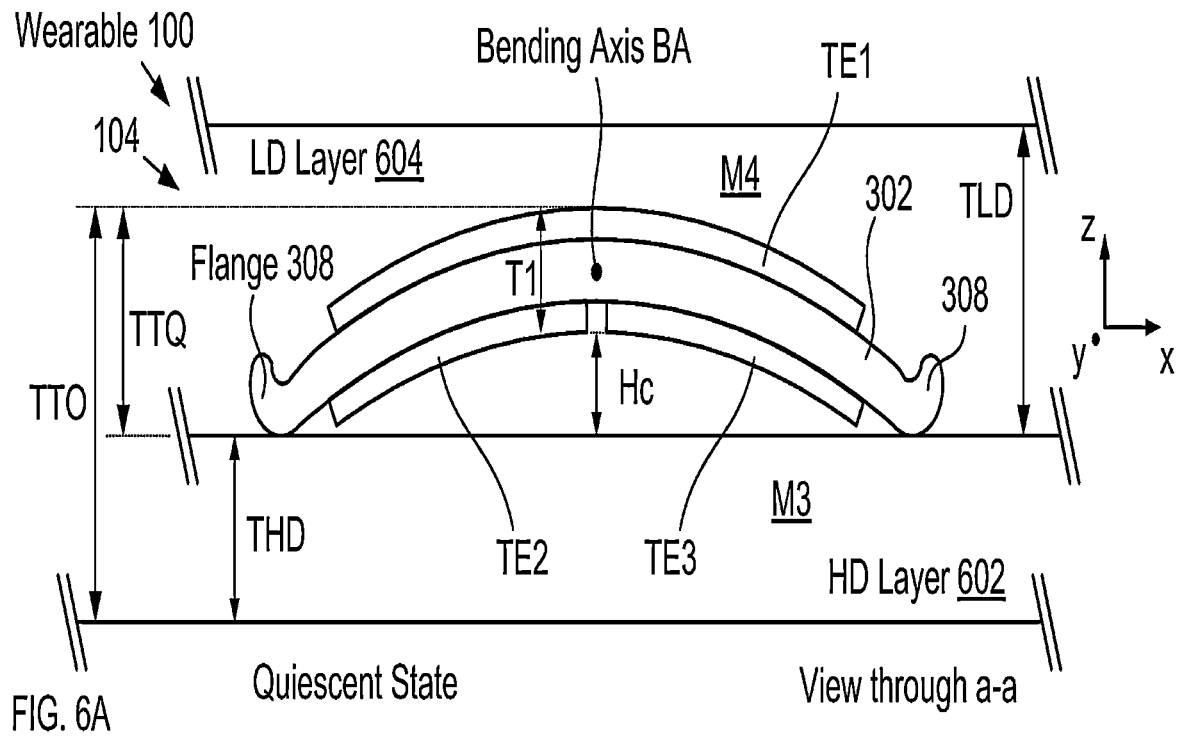
FIGS. 6A-B depict schematic drawings of simplified sectional views of a region of completed wearable 100 in its quiescent and deformed states, respectively.
Figure 6B:
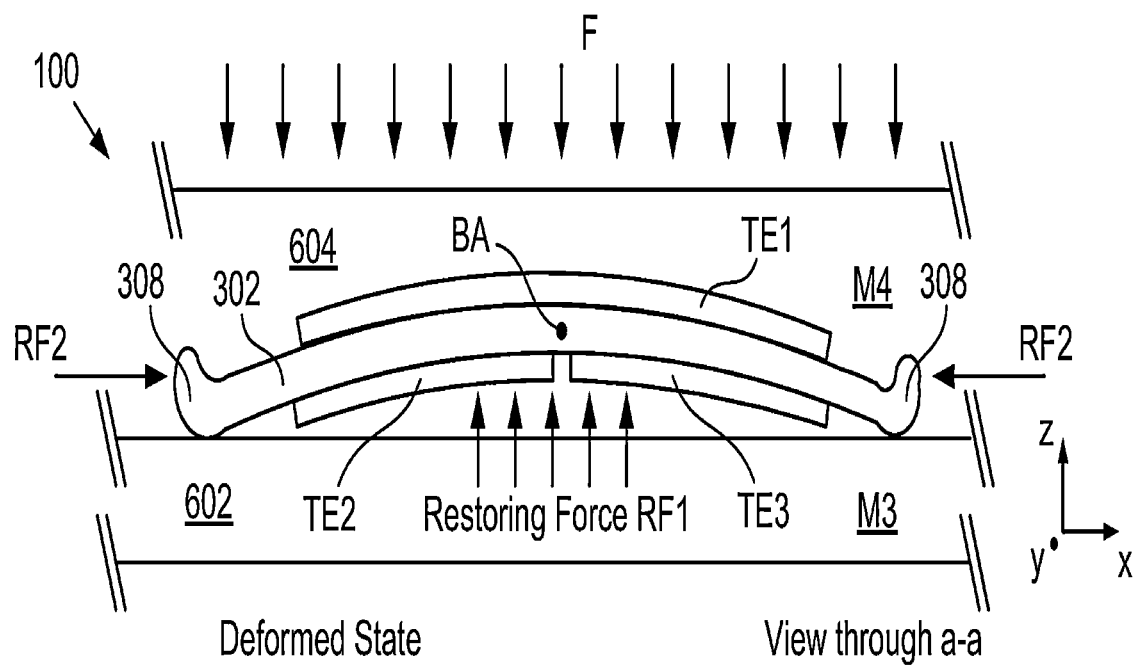

FIGS. 6A-B depict schematic drawings of simplified sectional views of a region of completed wearable 100 in its quiescent and deformed states, respectively. The sectional views of transducer 104 are taken through line a-a, as depicted in FIG. 3A.

In the depicted example, insole body 102 includes a pair layers of material having different mechanical properties—HD layer 602, which is located below transducers 104, and LD layer 604, which completely surrounds the transducers and electrical components. Preferably, HD layer 602 is formed prior to operation 201. When transducer 104 is in its quiescent state, HD layer 602 has thickness THD and LD layer 604 has thickness TLD.

HD layer 602 comprises material M3, which has a relatively higher density, while LD layer 604 comprises material M4, which has a relatively lower density. In the depicted example, material M3 is a high-density polyurethane (PU) and material M4 is a low-density polyurethane; however, a wide range of materials are suitable for use in either of HD layer 602 and LD layer 604.

It is an aspect of the present disclosure that the two-layer structure of insole body 102 fosters bending-strain-based operation of transducers 104. It should be noted, however, that one or both of materials M3 and M4 can include any suitable material, such as a monolayer of polyurethane, mono- or multi-layers of viscoelastic gels, neoprene rubbers, foams, and the like without departing from the scope of the present disclosure.

As will be apparent to one skilled in the art, insole thickness can vary over quite a large range, depending upon the specific type of insole. The preferred thicknesses of HD layer 602 and LD layer 604, therefore, are based on the particular type of insole application for which wearable 100 is intended.

Table 1 below shows approximate thicknesses in the heel and ball areas of the foot for different types of conventional insoles.

TABLE 1

Representative dimensions for typical insole types.

| Type of Conventional Insole | Thickness at Heel (mm) | Thickness at Ball of Foot (mm) |
|---|---|---|
| Orthotic | 10 | 4.5 |
| Non-orthotic | 3.5 | 2.5 |
| Military Boot | 3.5 | 2.5 |
| Sports Shoe | 3 | 2 |

The total operational thickness, TTO, of transducer 104 within wearable 100 is equal to the sum of THD and the total quiescent thickness TTQ (i.e., transducer thickness, T1 and the height, Hc, of cavity 310 when the transducer is in its quiescent shape). As noted above, wearable 100 is an orthotic insole, which sets an upper bound on the value of TTO. In the depicted example, TLD is approximately 1 mm, THD is 2 mm, T1 is approximately 0.612 mm, and Hc is approximately 0.9 mm (i.e., TTQ is approximately 1.5 mm), resulting in a TTO of only 2.5 mm; however, these values are merely exemplary and matters of design. As a result, TLD, THD, T1, and Hc can have any practical values without departing from the scope of the present disclosure. Furthermore, in some embodiments, transducers having different values of TTO are used in the heel and ball of foot regions.

When wearable 100 is subjected to force F (e.g., when foot pressure is applied to the insole), the applied force flattens the structure of transducer 104, thereby bending the transducer out of its quiescent shape to make it "flatter" and longer (in the x-direction). This bending of the transducer reduces its curvature about bending axis BA.

It should be noted that the curved shape of transducer 104 mitigates compression of piezoelectric layers 306A and 306B, themselves, in response to force F. In some embodiments, standoffs, such as posts, reside within the piezoelectric layers to mitigate their compression in response to an applied force. As will be appreciated by one skilled in the art, after reading this Specification, compression of a piezoelectric layer configured to operate in bending mode is undesirable, as it negatively affects the bending response of the transducer. Specifically, the output signal from a piezoelectric element is proportional to the charge it builds up in response to strain. While a piezoelectric element responds to bending with a negative charge buildup, while it responds to compression with a positive charge buildup. As a result, any compression of a bending-mode piezoelectric element will cancel out at least some, if not all, of its response to bending. Embodiments in accordance with the present disclosure, therefore, are afforded advantages over the prior art.

In some embodiments, transducer 104 includes features that project from one or both of its major surfaces to inhibit compression of piezoelectric layers 306A and 306B. In some embodiments, transducer 104 is mounted in a seat that inhibits compression of piezoelectric layers 306A and 306B. Some non-limiting examples of structures suitable for facilitating bending-mode operation of a piezoelectric transducer while simultaneously inhibiting compression of its piezoelectric materials are disclosed in detail in parent application U.S. patent application Ser. No. 17/373,690.

When transducer 104 is flattened, material M4 beneath the transducer is compressed. Since M4 is a resilient material, it provides restoring force RF1 that acts to return the transducer to its quiescent state once force F is removed.

In addition, as noted above, substrate 302 is configured such that its ends are shaped into flanges 308 which have greater surface area in the y-z plane. As a result, more material M4 is displaced along the x-direction when transducer 104 elongates as it is flattened. This laterally displace material M4 gives rise to additional restoring force RF2, thereby augmenting restoring force RF1.

Flanges 308 provide additional advantage because they reduce the chance of damage due to substrate 302 cutting into LD layer 504 or abrading HD layer 502, thereby improving the lifetime and reliability of wearable 100.

As noted above, the choices of materials and thicknesses of substrate 302 and piezoelectric layers 306A and 306B typically depend upon the application for which a transducer is designed and the desired performance parameters of the transducer. For example, the design of the depicted example can provide substantially maximum generation of energy per user step—even with a TTO of only 1.5-2.0 mm. In some cases, however, less energy generation is required, allowing for more latitude in transducer design. For example, a transducer having a 1000-micron-thick brass substrate, 200-micron-thick piezoelectric layers comprising PZT sol-gel material, and having a TTO of 4 millimeters can produce significant energy when employed in an orthotic insole.

Figure 7A:
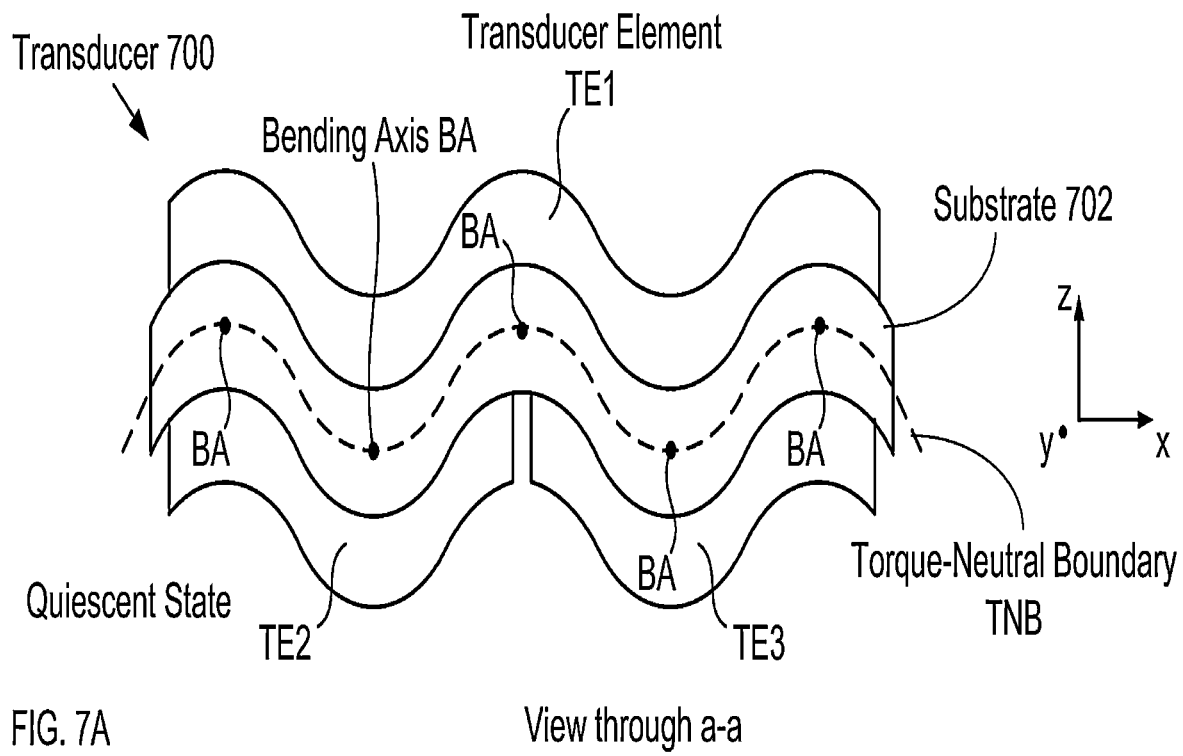
FIGS. 7A-B depict schematic drawings of sectional views of an alternative embodiment of a transducer, in its quiescent and deformed states, in accordance with the present disclosure.
Figure 7B:
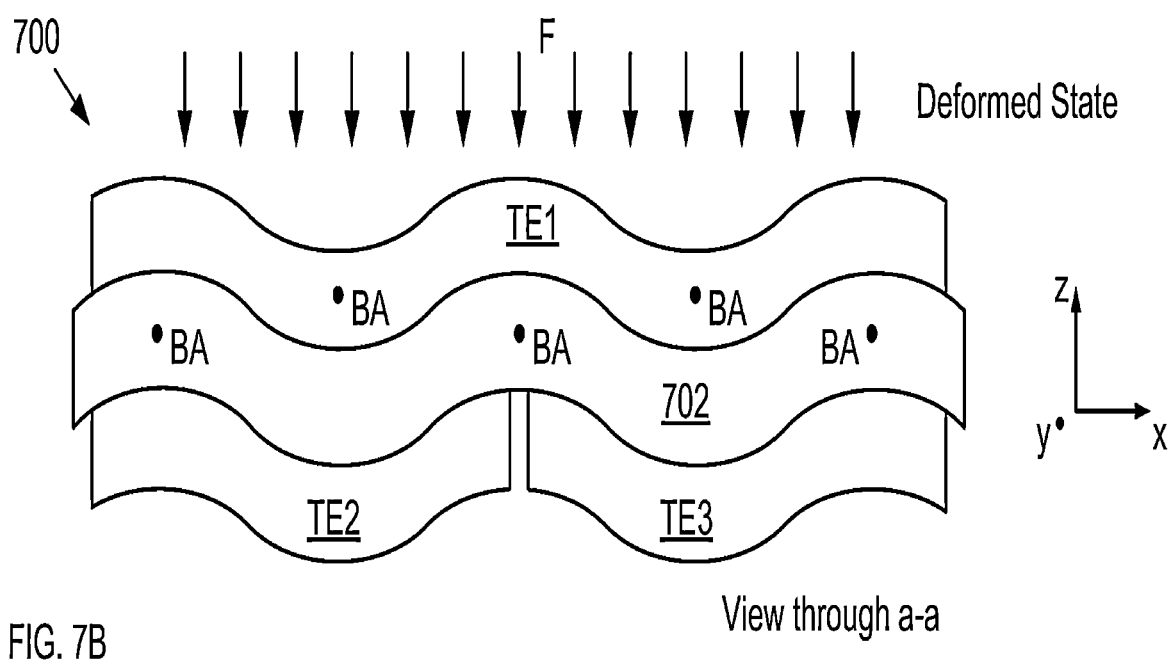

FIGS. 7A-B depict schematic drawings of sectional views of an alternative embodiment of a transducer, in its quiescent and deformed states, in accordance with the present disclosure. Transducer 700 is analogous to transducer 104; however, in transducer 700, substrate 702 is configured such that transducer 700 has a plurality of peaks and valleys arranged along the x-dimension when in its quiescent state, thereby giving rise to a "ruffled transducer."

Each peak and valley of transducer 700 is substantially aligned with a different bending axis BA. In some embodiments, a ruffled transducer is shaped such that it has peaks and valleys along two dimensions (e.g., the x- and y-dimensions). In some embodiments, a ruffled transducer has a cross-section having a known curved shape along at least one dimension, such as sinusoidal, parabolic, catenary, and the like. In some such embodiments, the shape of transducer is defined such that strain is distributed substantially evenly along at least one dimension.

Figure 8:
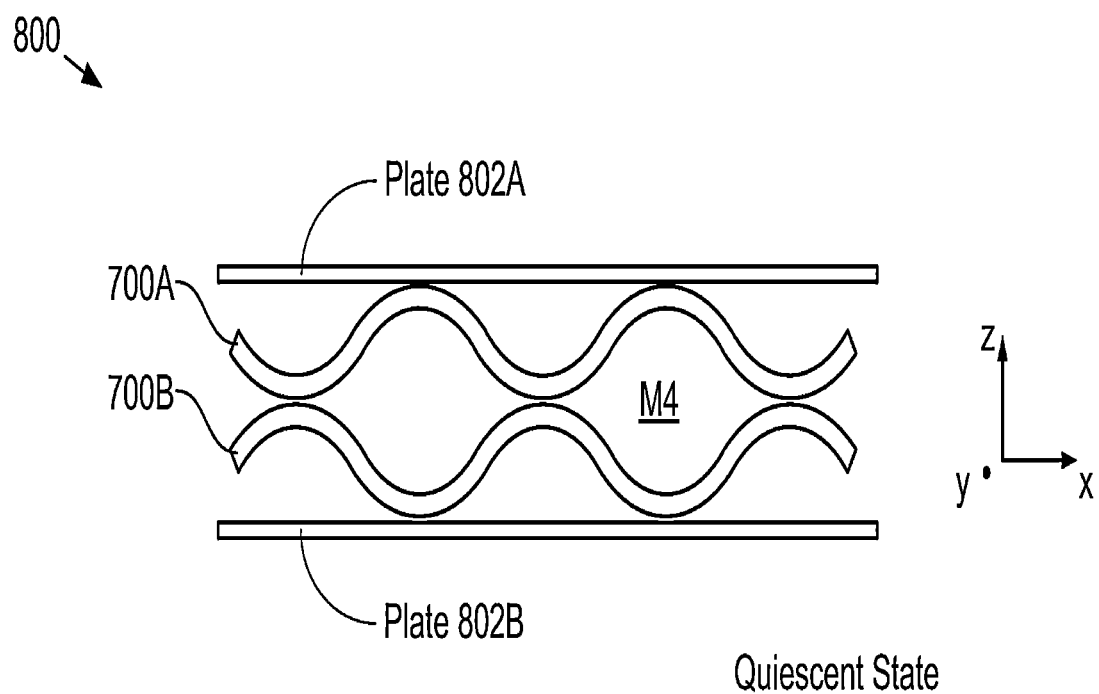
FIG. 8 depicts a schematic drawing of a sectional view of an alternative arrangement of transducers within a wearable in accordance with the present disclosure.

FIG. 8 depicts a schematic drawing of a sectional view of an alternative arrangement of transducers within a wearable in accordance with the present disclosure. Wearable 800 includes transducers 700A and 700B, plates 802A and 802B, and material M4.

Plates 802A and 802B are substantially rigid plates of structural material (e.g., metal, plastic, etc.), which are configured to substantially uniformly transfer an applied force to transducers 700A and 700B.

Wearable 800 is configured such that each of transducers 700A and 700B will be compressed by force F, thereby substantially doubling the magnitude of the output signals from their transducer elements.

In some embodiments, transducer 104 is configured such that an applied force causes it to stretch and/or bend like a cantilever element in one or more dimensions. A stretchable transducer is particularly well-suited for use in wearable applications such as an energy-scavenging strap that powers a bra, a belt, a chest strap, stretchy pants, a backpack, and the like.

Figure 9A:
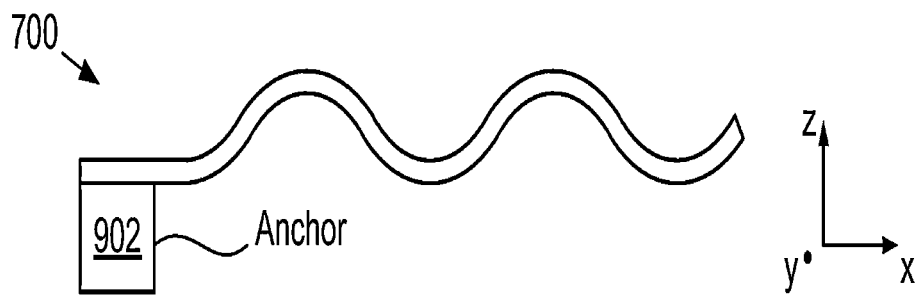
FIGS. 9A-C depict schematic drawings of cross-sectional views of a cantilevered ruffled transducer under different force conditions in accordance with the present disclosure.
Figure 9B:
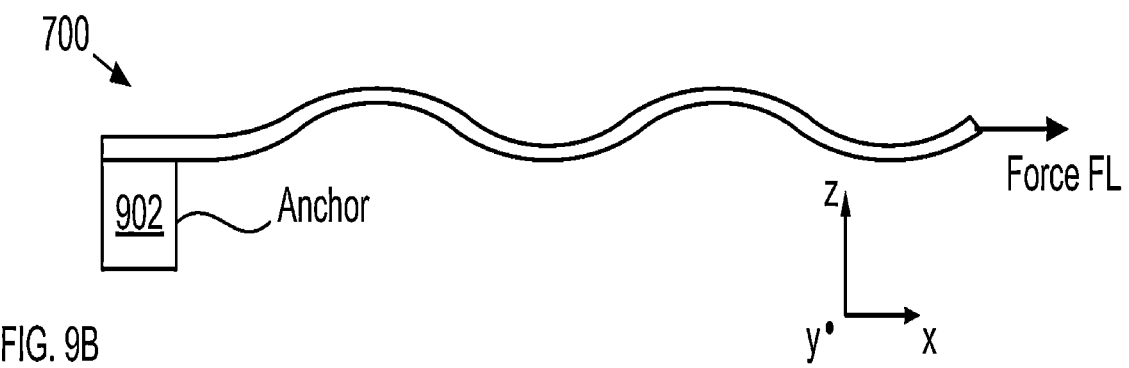
Figure 9C:
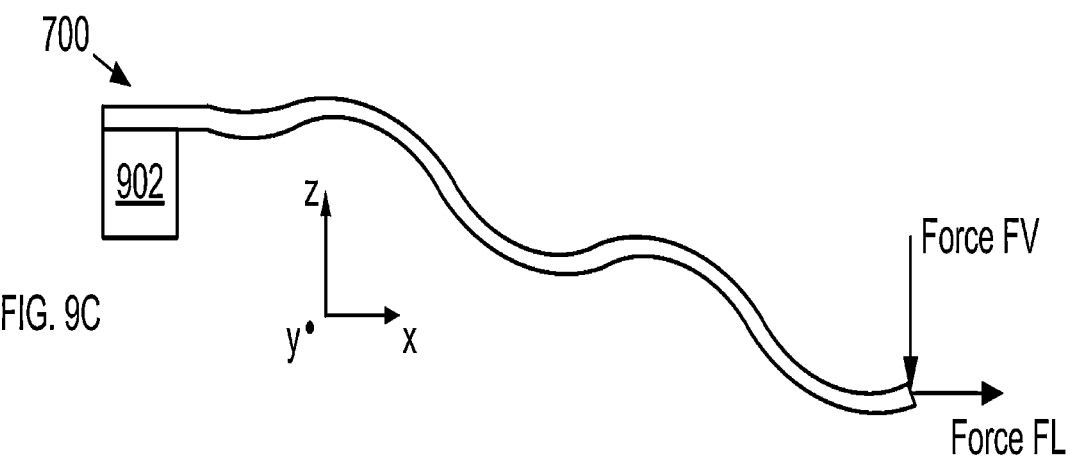
Figure 10A:
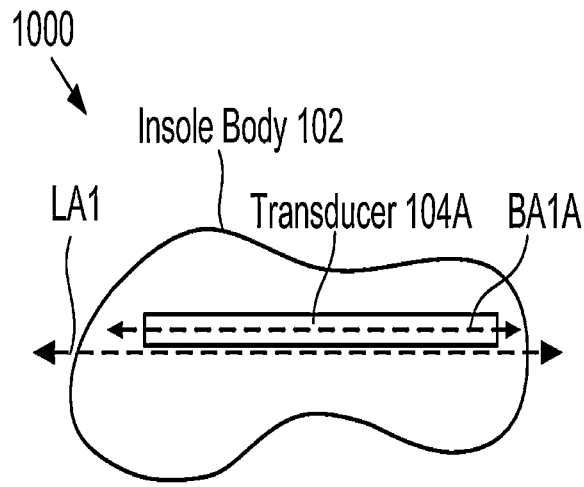
FIGS. 10A-D depict schematic drawings of cross-sectional views of wearables having alternative arrangements of bimorph transducers within a wearable in accordance with the present disclosure.
Figure 10B:
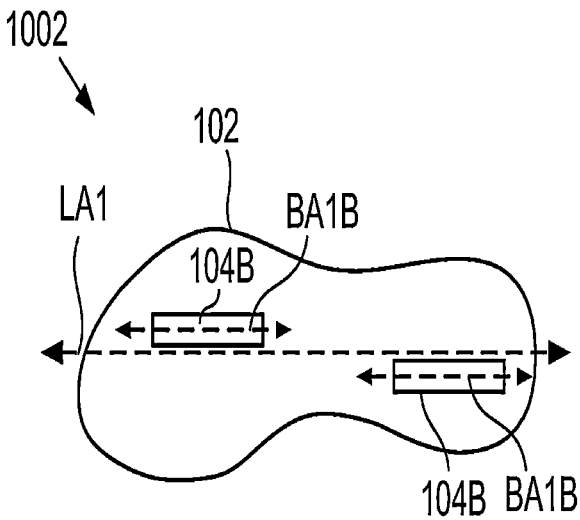
Figure 10C:
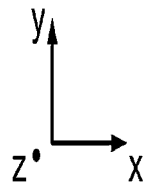
Figure 10C:
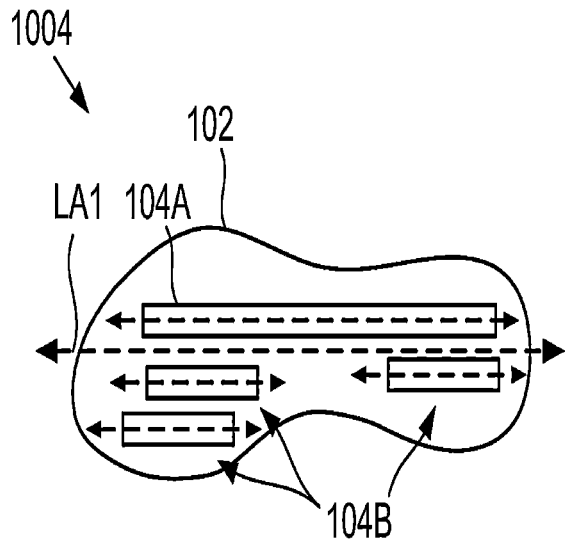
Figure 10D:
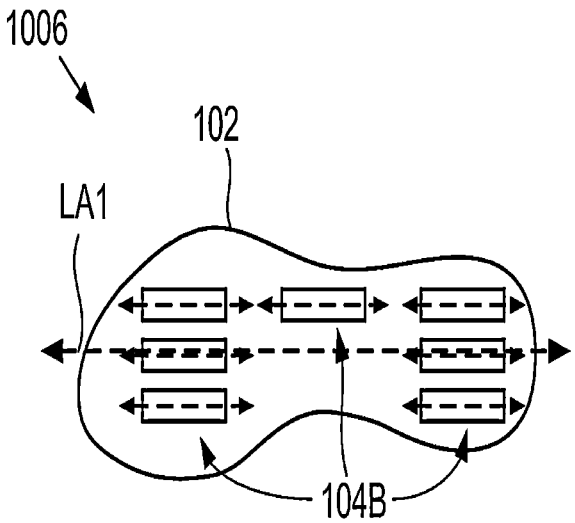

FIGS. 9A-C depict schematic drawings of cross-sectional views of a cantilevered ruffled transducer under different force conditions in accordance with the present disclosure.

In FIG. 9A, transducer 700 is depicted in its quiescent state while affixed to anchor 902. In other words, transducer 700 is depicted without any applied force.

In FIG. 9B, transducer 700 is depicted in a stretched state in response to applied force FL, which is a lateral force directed only along the x-direction. As transducer 700 is stretched along the x-axis, the transducer is deformed from its quiescent shape by being pulled into a flatter profile.

In FIG. 9C, transducer 700 is depicted in a stretched state in response to applied forces FL and FV, which are lateral and vertical forces directed along the x- and y-directions, respectively.

FIGS. 10A-D depict schematic drawings of cross-sectional views of wearables having alternative arrangements of bimorph transducers within a wearable in accordance with the present disclosure. Each of wearables 1000, 1002, 1004, and 1006 is analogous to wearable 100 and comprises insole body 102 and one or more transducers analogous to transducer 104. It should be noted that, for clarity, only transducers 104 and their respective bending axes are shown in FIGS. 10A-D.

Wearable 1000 includes transducer 104A, which is a long version of transducer 104 and arranged within insole body 102 such that bending axis BA1A is aligned with longitudinal axis LA1. As a result, transducer 104A can generate voltage and energy in response to a rolling motion of the user's foot, as well as during each step as the shoe meets the ground or lifts from it.

Wearable 1002 includes a pair of transducers 104B, each of which is a short version of transducer 104. Transducers 104B are arranged within insole body 102 such that each of their bending axes BA1B is aligned with longitudinal axis LA1. Although the depicted example includes two transducers that are displaced from longitudinal axis LA1, in some embodiments, the bending axis of at least one transducer is colinear with the longitudinal axis of its wearable.

Wearable 1004 includes a combination of transducers that includes one transducer 104A and a pair of transducers 104B. Transducers 104A and 104B are arranged within insole body 102 such that each of their bending axes BA1A and BA1B is aligned with longitudinal axis LA1.

Wearable 1006 includes a plurality of transducers 104B, which is arranged within insole body 102 such that each of their bending axes BMA and BA1B is aligned with longitudinal axis LA1. The arrangement of transducers includes two linear arrays located approximately at the heel and ball-and-foot areas of the insole body, as well as a single transducer 104B located near the arch region of the insole body.

In some embodiments, a wearable includes transducers whose bending axes are aligned along different directions (e.g., some along the x-axis and some along the y-axis, at different angles with respect to at least one of the x- and y-axes, etc.). In some embodiments, a wearable includes a mixture of transducer types, such as any combination of ruffled, waffled, channel, and/or circular transducers.

Figure 11:
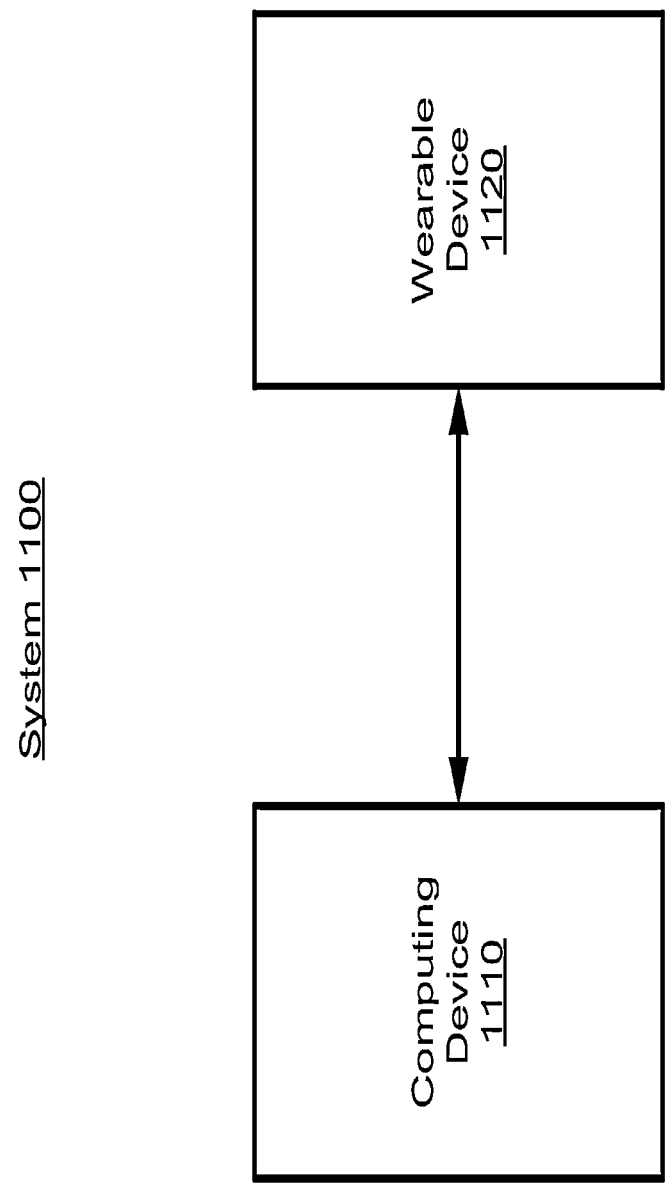
FIG. 11 depicts a block diagram of a system comprising a computing device and a wearable device, in accordance with one embodiment of the present disclosure.

FIG. 11 depicts a block diagram of a system 1100 in accordance with one embodiment of the present disclosure. As shown in the figure, system 1100 comprises a computing device 1110 and a wearable device 1120. Computing device 1110 may be a smartphone, a tablet, a laptop computer, a desktop computer, etc. that is equipped with a touchscreen and is capable of executing a graphical user interface (GUI). Wearable device 1120 may be, for example, an embodiment of a wearable disclosed in this application (e.g., an embodiment of wearable 100, an embodiment of wearable 1000, an embodiment of wearable 1002, an embodiment of wearable 1004, an embodiment of wearable 1006, etc.); a smart watch such as an Apple Watch® or Google Pixel Watch®; a fitness tracker such as a Fitbit® or Amazon Halo View®; etc. As shown in the figure, computing device 1110 and wearable device 1120 communicate bi-directionally. In some embodiments, the communication might be via a short-range wireless technology such as Bluetooth, Bluetooth Low Energy [BLE], Zigbee, etc., while in some other embodiments the communication might be via a wireless local area network (LAN) technology such as Wi-Fi, while in yet other embodiments the communication might be via a wired connection such as Universal Serial Bus [USB] or Ethernet.

Figure 12:
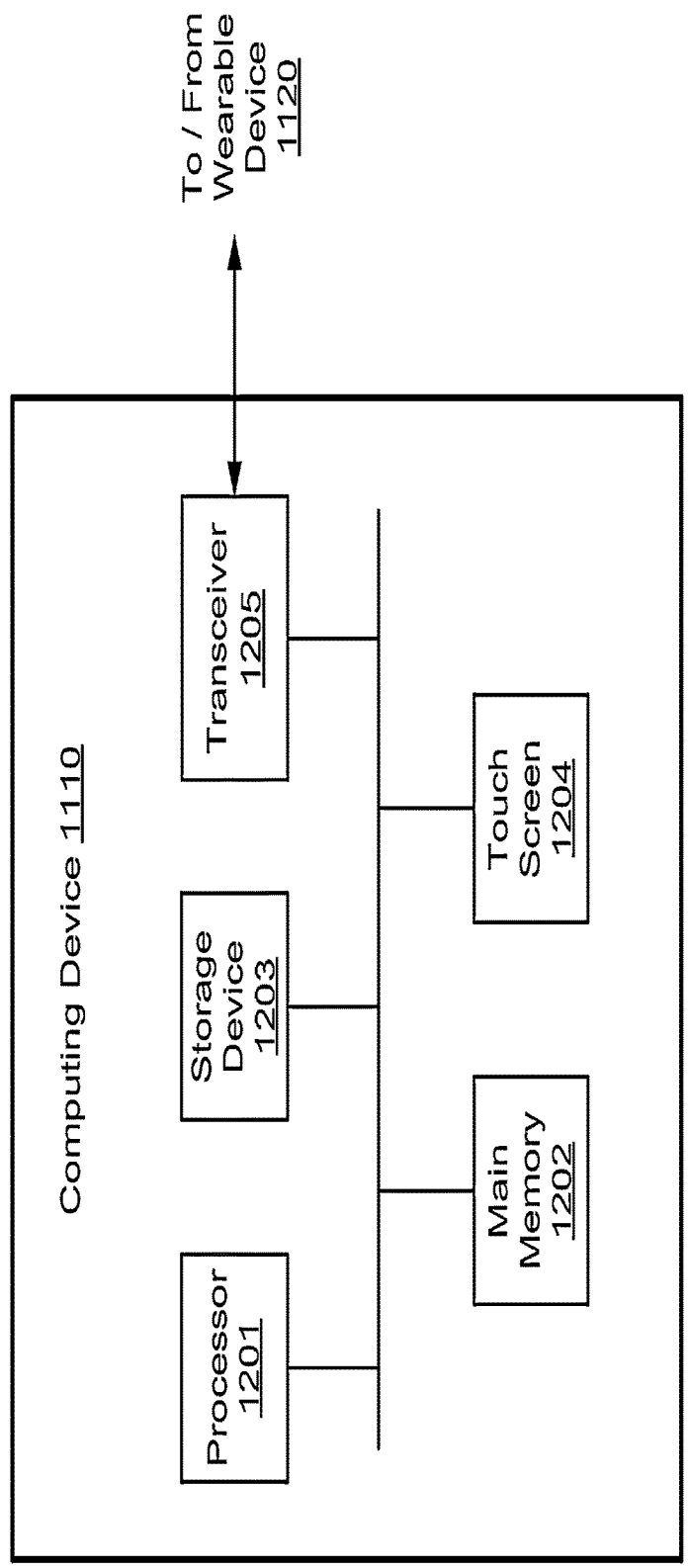
FIG. 12 depicts a block diagram of salient elements of computing device 1110, as shown in FIG. 11, in accordance with one embodiment of the present disclosure.

FIG. 12 depicts a block diagram of computing device 1110 operating in accordance with aspects and implementations of the present disclosure. Computing device 1110 may be a smartphone, a tablet, a laptop computer, a desktop computer, or any other computing or communication device. As shown in FIG. 12, computing device 1110 comprises processor 1201, main memory 1202, storage device 1203, touch screen 1204, and transceiver 1205, interconnected as shown (e.g., via one or more busses, etc.).

Processor 1201 represents one or more general-purpose processing devices such as a microprocessor, central processing unit, or the like. More particularly, processor 1201 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. Processor 1201 may also be one or more special-purpose processing devices such as an application specific integrated circuit (ASIC), a field programmable gate array (FPGA), a digital signal processor (DSP), network processor, or the like. Processor 1201 is capable of executing instructions stored in main memory 1202 and storage device 1203, including instructions for executing an implementation of GUI 1500, as described below; of reading data from and writing data into main memory 1202 and storage device 1203; of receiving input signals from and transmitting output signals to touch screen 1204; and of receiving input signals from and transmitting output signals to transceiver

1205. While a single processor is depicted in FIG. 12 for simplicity, computer system 1200 might comprise a plurality of processors.

Main memory 1202 is capable of storing executable instructions and data, including instructions and data for executing an implementation of GUI 1500, and may include volatile memory devices (e.g., random access memory [RAM]), non-volatile memory devices (e.g., flash memory), and/or other types of memory devices.

Storage device 1203 is capable of persistent storage of executable instructions and data, including instructions and data for executing GUI 1500, and may include a magnetic hard disk, a Universal Serial Bus [USB] solid state drive, a Redundant Array of Independent Disks [RAID] system, a network attached storage [NAS] array, etc. While a single storage device is depicted in FIG. 12 for simplicity, computing device 1110 might comprise a plurality of storage devices.

Touch screen 1204 is a combination of a display device (e.g., an LCD display, an AMOLED display, an OLED display, etc.) and a touch panel input device. In accordance with one embodiment, touch screen 1204 is capable of displaying GUI 1500 and receiving inputs to GUI 1500 via user touch (e.g., presses, gestures, etc.).

Transceiver 1205 is capable of transmitting signals to and receiving signals from wearable device 1120, as well as to/from other computing and communications devices. Transceiver 1205 is further capable of receiving signals from processor 1201 (e.g., requests and/or data to be transmitted to wearable device 1120, etc.), and of transmitting signals to processor 1201 (e.g., data received from wearable device 1120, etc.) It should be noted that depending on the particular application programming interface (API) provided by wearable device 1120 and the terminology that the API employs, functionality of the API (e.g., taking a measurement, providing measurement data, etc.) might be invoked via "instructions" rather than "requests." For the purposes of this specification, the term "requests" will be used to encompass instructions as well as requests.

In one embodiment, transceiver 1205 transmits and receives wireless signals (e.g., via Bluetooth, Bluetooth Low Energy [BLE], Zigbee, Wi-Fi, cellular, satellite, etc.). In some other embodiments, transceiver 1205 might communicate over a wired connection, such as USB or Ethernet. In still other embodiments, computing device 1110 might comprise a plurality of transceivers (e.g., a wireless transceiver and a wireline transceiver, etc).

Figure 13:
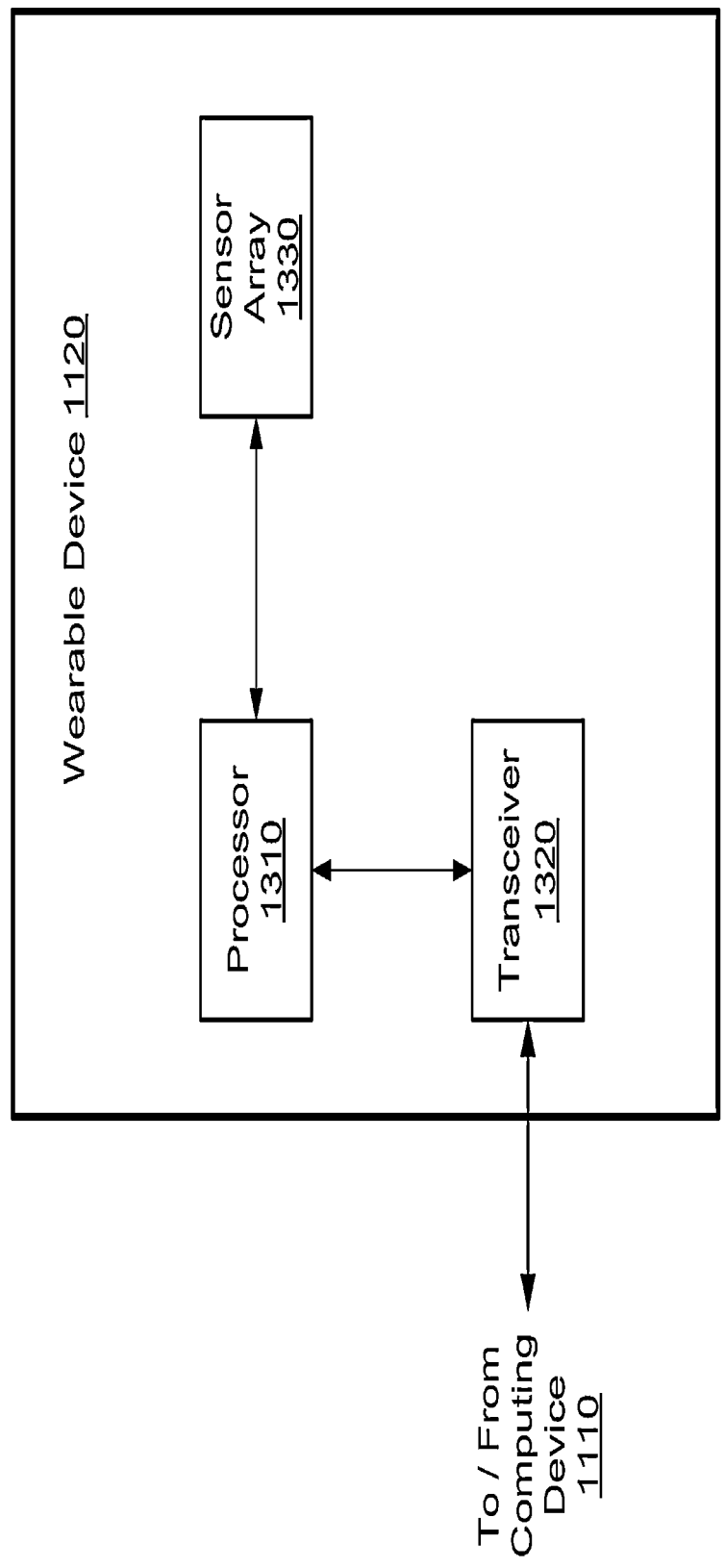
FIG. 13 depicts a block diagram of salient elements of wearable device 1120, as shown in FIG. 11, in accordance with one embodiment of the present disclosure.

FIG. 13 depicts a block diagram of salient elements of wearable device 1120, in accordance with one embodiment of the present disclosure. As shown in the figure, wearable device 1120 comprises a processor 1310, a transceiver 1320, and a health/fitness sensor array 1330, interconnected as shown.

Processor 1310 is capable of receiving measurement data from health/fitness sensor array 1330; of processing measurement data (e.g., estimating calories burned based on heart rate, estimating respiratory rate based on heart rate, etc.); of providing an application programming interface (API) for invoking functions of wearable device 1120; of transmitting data and/or requests to health/fitness sensory array 1330 (e.g., a request to take one or more measurements, a request to provide measurement data, etc.); of providing data and/or requests to transceiver 1320 for transmission (e.g., to computing device 1110, etc.), and of receiving data and/or requests from transceiver 1320 (e.g., data and/or requests from computing device 1110, etc.). In one embodiment, processor 1310 comprises a real-time clock that enables processor 1310 to know the time, day, and date at each moment.

Transceiver 1320 is capable of transmitting signals (e.g., to computing device 1110, etc.), of receiving signals (e.g., from computing device 1110, etc.), and of communicating with processor 1310.

Health/fitness sensor array 1330 is capable of obtaining measurements of parameters such as body temperature, blood oxygen, heart rate, steps taken, etc.; of providing measurement data to processor 1310; and of receiving data and/or requests from processor 1310 (e.g., requests to take measurement(s), etc.). In some embodiments, health/fitness sensor array 1330 may comprise one or more elements in common with sensor module 106 disclosed above.

Figure 14:
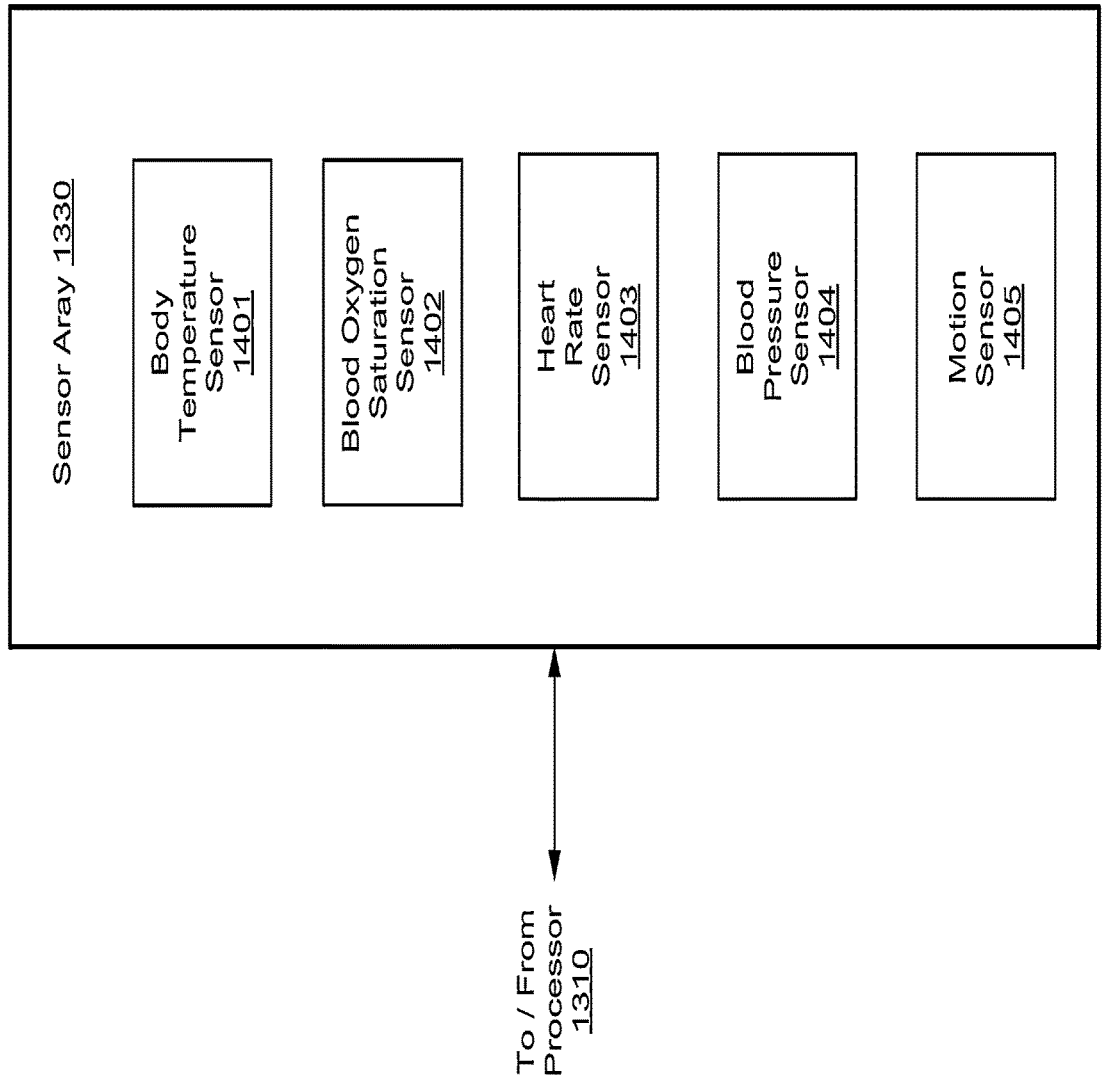
FIG. 14 depicts a block diagram of salient elements of health/fitness sensor array 1330, as shown in FIG. 13, in accordance with one embodiment of the present disclosure.

FIG. 14 depicts a block diagram of salient elements of health/fitness sensor array 1330, in accordance with one embodiment of the present disclosure. As shown in the figure, health/fitness sensor array 1330 comprises a body temperature sensor 1401, a blood oxygen saturation sensor 1402, a heart rate sensor 1403, a blood pressure sensor 1404, and a motion sensor 1405. In one embodiment, motion sensor 1405 is a three-dimensional micro-electro-mechanical systems ("MEMS") accelerometer/gravimetric sensor, similar to the multi-axis accelerometer of wearable 100 disclosed above. It should be noted that in some embodiments, health/fitness sensor array 1330 might employ one or more sensors that are capable of measuring a plurality of parameters (e.g., a pulse oximeter capable of measuring both blood oxygen saturation and heart rate, etc.). It should be further noted that in some embodiments, health/fitness sensor array 1330 might further comprise other types of sensors not depicted in FIG. 14.

Figure 15:
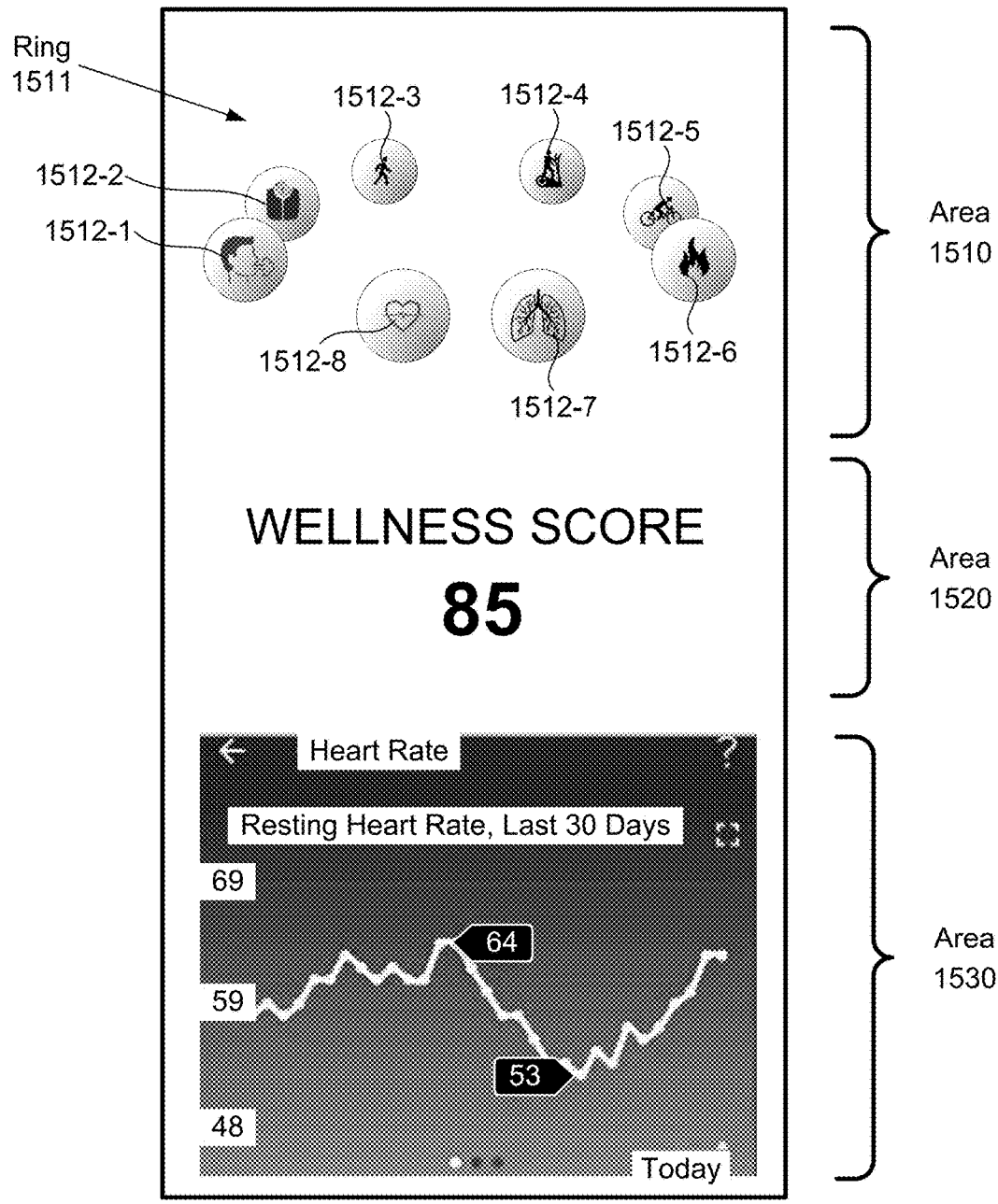
FIG. 15 depicts a graphical user interface (GUI) in accordance with one embodiment of the present disclosure.

FIG. 15 depicts a graphical user interface (GUI) 1500, in accordance with one embodiment of the present disclosure. In one example, GUI 1500 executes on computing device 1110, enabling a user to interact with wearable device 1120 via computing device 1110.

GUI 1500 is capable of displaying text, images, and graphical elements such as icons and buttons, and of receiving user input via a touch screen (e.g., a gesture performed by a user, such as a swipe or a pinch; a press of a graphical element; etc.). As shown in the figure, GUI 1500 comprises three areas 1510, 1520 and 1530. Area 1510 displays a plurality of icons arranged in a ring (a "globe carousel"), as described in detail below. Area 1520 displays an overall "wellness" score, which may be a composite of a plurality of health/fitness parameters. Area 1530 displays historical parameter data (e.g., body temperature measurements over the last two weeks, heart rate measurements over the last six hours, etc.). In one embodiment, the historical parameter data is obtained from wearable device 1120.

As shown in FIG. 15, area 1510 displays a three-quarter view of a ring 1511 of icons 1512-1 through 1512-8. As will be appreciated by those skilled in the art, the number of icons in the ring is merely illustrative; in some embodiments there might be fewer than eight icons, or more than eight icons.

In one embodiment, each icon 1512-*i* is associated with a particular health/fitness parameter, such as body temperature, heart rate, blood oxygen saturation, blood pressure, respiratory rate, steps taken, traveling speed (e.g., walking speed, running speed, crawling speed, speed while engaging in sports or other activities, etc.), distance traveled, calories burned, etc. In one implementation, each icon 1512-*i* pictorially conveys the particular health/fitness parameter with which it is associated (e.g., an icon depicting a heart and signal for heart rate, an icon depicting lungs for respiratory rate, etc.). In one example, health/fitness parameter values are obtained from wearable device 1120.

In one implementation, each of icons 1512-1 through 1512-8 is depicted inside a respective two-dimensional projection of a sphere (or "globe"), which is rendered as a circle with light shading, as shown in the figure. Because the ring is rendered in perspective, the globes in the front (or "lower") portion of the ring appear larger than the icons in the rear (or "upper") portion of the ring. As will be appreciated by those skilled in the art, in some other implementations, one or more of icons 1512 might be depicted inside a different type of shape/object (e.g., an unshaded circle, an ellipse, a square, a projection of a cube, etc.), rather than inside a projection of a sphere, while in yet other implementations, one or more of icons 1512 might be depicted on their own, without any surrounding shape/object.

In one implementation, the background of each icon 1512-*i* is displayed in a color reflecting a state of the associated health/fitness parameter. In examples where an icon is displayed within a shape/object (e.g., a globe, etc.), the background is the shape/object, and the background color is a fill color of the shape/object. It should be noted that while in FIG. 15 the backgrounds of icons 1512 are depicted in gray scale, and are the same shade of gray, this in no way limits the use of color or variations in shades of gray/black/white in embodiments of GUI 1500.

In one example, the background color of an icon 1512-*i* is: (1) green when (a) the value of an associated health/fitness parameter value, such as heart rate or blood oxygen saturation, is in a normal range, or when (b) the value of an associated health/fitness parameter, such as calories burned, is considered "good" with respect to one or more criteria; (2) yellow when (a) the value of an associated health/fitness parameter is in a borderline normal range approaching an abnormal and/or dangerous range, or is considered "ok but not good," "mediocre," "neutral," etc. with respect to one or more criteria; (3) red when the value of an associated health/fitness parameter is in an abnormal range, or is considered "bad," "dangerous," etc. with respect to one or more criteria. As will be appreciated by those skilled in the art, in some examples one or more of the normal/abnormal ranges, and/or what is considered good/dangerous/etc. for a particular parameter, and/or the criteria for determining what is considered good/dangerous/etc., might be user-specific, while in other examples they might be the same for all users.

As will further be appreciated by those skilled in the art, some embodiments of the present disclosure might characterize health/fitness parameter values using an alternative background color scheme. In implementations where there are no shapes/objects surrounding icons, colors might be assigned to the icons themselves, rather than their backgrounds. As will further be appreciated by those skilled in the art, some embodiments of the present disclosure might convey parameter values using one or more alternative types of visual schemes, either instead of color, or in addition to color (e.g., changing the size of an icon, changing the size of the surrounding shape, changing the orientation of an icon, animating an icon in some fashion, etc.)

As disclosed above, area 1520 displays an overall "wellness" score, which might be a composite of a plurality of the health/fitness parameters. In one embodiment, the wellness score takes into account heart rate, blood oxygen saturation, blood pressure, and respiratory rate, such that a high score indicates good health. In one implementation, the wellness score is an integer with a maximum value of 100, where 100 means that every parameter taken into account in the wellness score is in normal range or is "good," as described above.

Area 1530 displays historical parameter data (e.g., body temperature measurements over the last two weeks, heart rate measurements over the last six hours, etc.). In one embodiment, the historical parameter data is obtained from wearable device 1120. As described in detail below, the particular health/fitness parameter that is displayed in area 1530 is determined by user input to touch screen 1204, and more particularly, to user touches/gestures in area 1510.

In accordance with embodiments of the present disclosure, a user can interact with GUI 1500, and can interact with wearable device 1120 via GUI 1500, in a variety of ways.

In one embodiment, the depiction of ring 1511 in area 1510 is responsive to user input, such that when a user performs a left-to-right swiping gesture across some or all of the front portion of ring 1511, the ring 1511 rotates counterclockwise, in animated fashion. The rotation appears as icons 1512 traveling around the center of ring 1511, in a manner similar to orbiting planets or satellites. Similarly, when a user performs a right-to-left swiping gesture across some or all of the front portion of ring 1511, ring 1511 rotates clockwise. In some implementations, GUI 1500 may also rotate ring 1511 in response to a swiping gesture below the front portion of ring 1511 (e.g., in the lower portion of area 1510 below ring 1511, etc.), in a manner similar to a swiping gesture across some or all of the front portion of ring 1511.

In one embodiment, ring 1511 may also rotate in response to a swiping gesture across some or all of the rear portion of ring 1511 (e.g., a clockwise rotation in response to a left-to-right swiping gesture across some or all of the rear portion of ring 1511, a counterclockwise rotation in response to a right-to-left swiping gesture across some or all of the rear portion of ring 1511, etc.). Further, in some implementations ring 1511 may rotate in response to a swiping gesture above the rear portion of ring 1511 (e.g., in the upper portion of area 1510 above ring 1511, etc.), in a manner similar to a swiping gesture across some or all of the rear portion of ring 1511.

In one embodiment, GUI 1500 further enables a user to interact with GUI 1500, and with wearable device 1120 through GUI 1500, via pressing of one or more icons 1512. In some implementations, GUI 1500 may be responsive to presses of icons in the front portion of ring 1511 only, while in some other implementations, GUI 1500 may be responsive to presses of all icons 1512, regardless of their location in ring 1511.

In accordance with one embodiment, when a user presses a particular icon 1512-*i*, historical data for the associated health/fitness parameter for the user (e.g., one or more prior measurements for the user, etc.) during a particular time period (e.g., the last 30 minutes, the last four hours, the last three days, the last week, the last month, a prior time period [e.g., a prior day, a prior week, a prior month, etc.], etc.) is displayed in area 1430 (e.g., as a line graph, as a bar graph, as a table, etc.). In one embodiment, the historical data is obtained from wearable device 1120.

In some implementations, the time period might be a fixed value specified a priori (e.g., ten minutes, one hour, etc.), while in some other implementations the time period may have a default value that can be changed by a user (e.g., via a settings menu, etc.). For the latter case, in some examples a user might specify the time period via a selection among possible choices, while in other examples a user might enter a particular desired numerical value. As will be appreciated by those skilled in the art, in some implementations each health/fitness parameter might have its own time period (e.g., ten minutes for heart rate, 30 minutes for blood pressure, etc.), while in other implementations there might be a single time period for all parameters.

As noted above, in some implementations the historical data might be displayed as a graph (e.g., a line graph, a bar graph, etc.), while in some other implementations the historical data might be displayed in some other fashion (e.g., as a table, etc.). In the example depicted in FIG. 15, GUI 1500 displays the historical data as a line graph. In one implementation, one or more of the points on the graph may be labeled with the associated numerical value. In some examples, it may be desirable to include the most recent parameter measurement in the labeled point(s).

As will be appreciated by those skilled in the art, in some implementations the manner in which historical data is displayed might differ among parameters (e.g., a graph for heart rate, a table for blood pressure, etc.), while in other implementations there might be one type of data presentation for all parameters. As will further be appreciated by those skilled in the art, in some implementations the manner in which historical data is presented might be selectable by a user. Further, in some implementations, GUI 1500 might be capable of displaying historical data for a plurality of health/fitness parameters at the same time (e.g., a graph for one parameter underneath a graph for another parameter; two graphs side-by-side; a table for one parameter underneath a graph for another parameter; a graph and a table side-by-side, etc.).

In accordance with one embodiment, GUI 1500 enables further user interaction with GUI 1500 and wearable device 1120 via pressing-and-holding of icons. In one implementation, when a user presses an icon 1512-*i* and holds the press for at least N units of time, and optionally, for less than M units of time, where M>N (e.g., N=3 seconds and M=5 seconds, etc.), a request is sent to wearable device 1120 to take one or more measurements of the health/fitness parameter associated with icon 1512-*i* and return measurement data for that parameter to computing device 1110 (e.g., one or more of the measurement(s) themselves, one or more numeric values derived from the measurement(s), etc.). In this way, each icon provides two functions when pressed, where the particular function performed depends on the duration of the press. In some examples, the value of N also serves as a maximum duration threshold for "regular" (or "short") presses, such that a press lasting for less than N units of time is interpreted as a regular press, and a press lasting for at least N units of time (and optionally, for less than M units of time) is interpreted as a "long" press.

Accordingly, a regular press of an icon 1512-*i* results in GUI 1500 displaying historical data for the health/fitness parameter associated with that particular icon, as described above, and a long press of icon 1512-*i* results in computing device 1110 sending a request to wearable device 1120 to (1) take one or more measurements of the health/fitness parameter associated with icon 1512-*i*, and (2) return measurement data associated with that parameter to computing device 1110. In one embodiment, GUI 1500 displays the measurement data in area 1530, either by itself, or appended to historical data as the most recent value of the parameter (e.g., a graph in which the most recent measurement is the rightmost data point in the graph, a table in which the most recent measurement is the last entry in the table, etc.).

Figure 16:
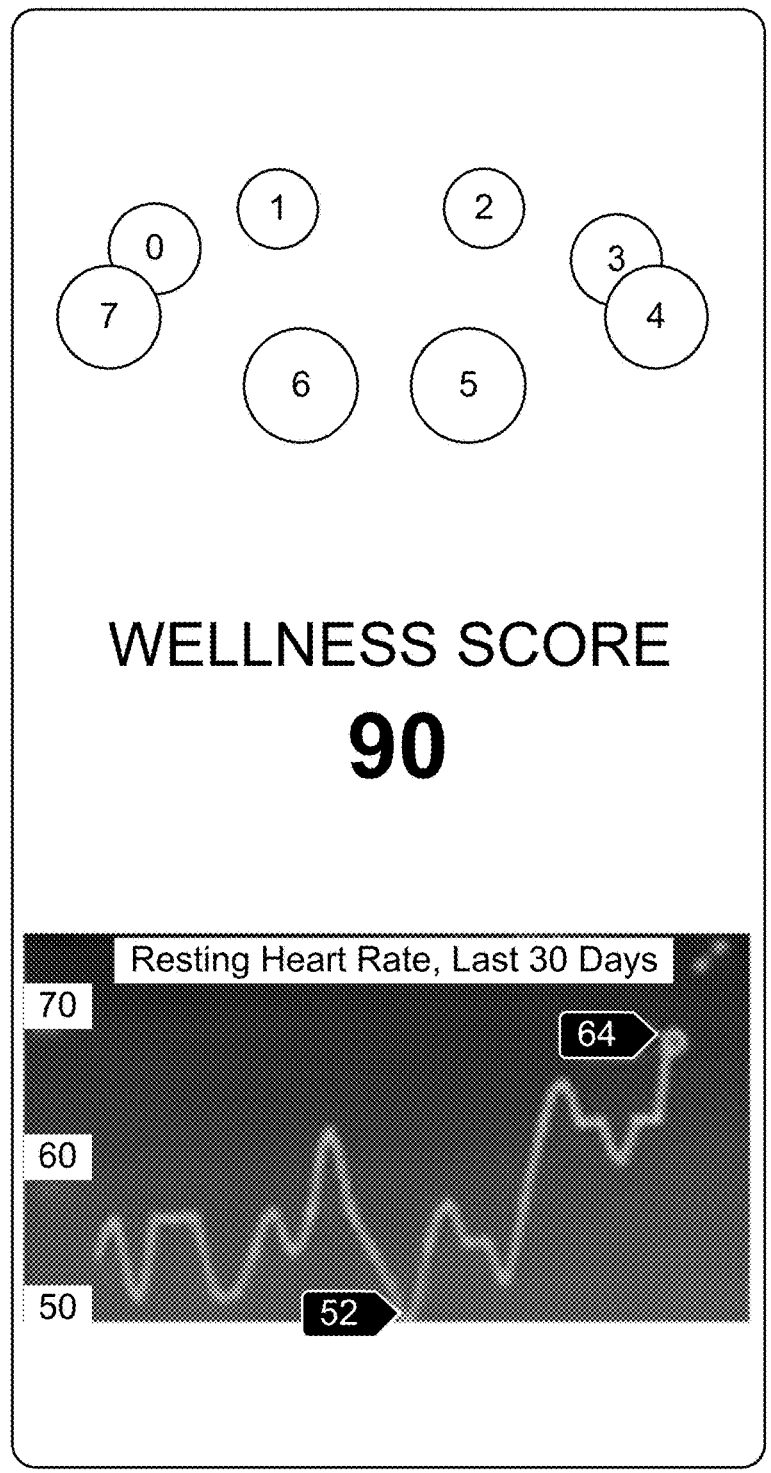
FIG. 16 depicts a first implementation of graphical user interface (GUI) 1500, as shown in FIG. 15, executing on a computing device, in accordance with one embodiment of the present disclosure.
Figure 17:
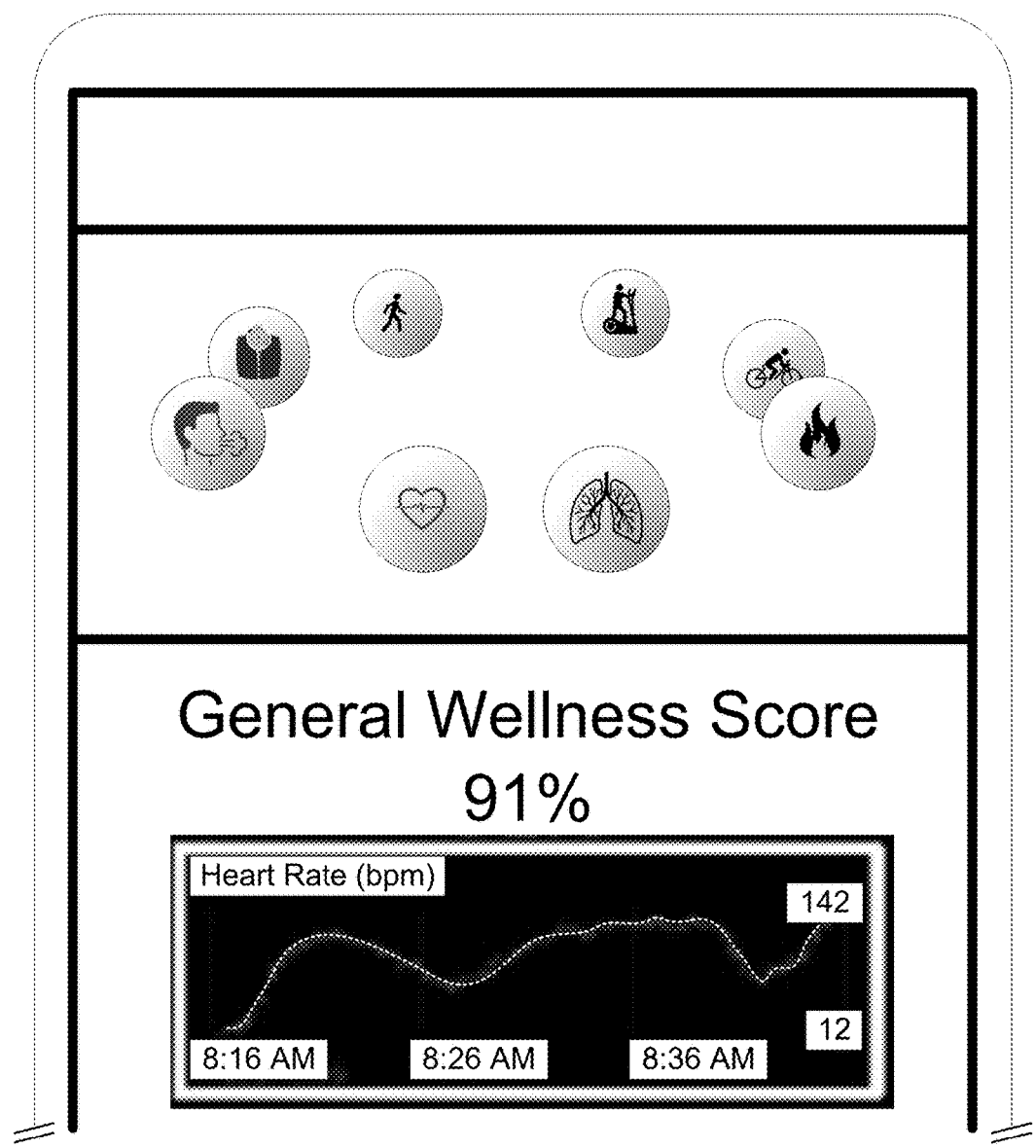
FIG. 17 depicts a second implementation of GUI 1500 executing on a computing device, in accordance with one embodiment of the present disclosure.

FIG. 16 depicts a first implementation of GUI 1500 executing on a computing device, in accordance with one embodiment of the present disclosure. In one example, the computing device is computing device 1110. FIG. 17 depicts a second implementation of GUI 1500 executing on a computing device, in accordance with one embodiment of the present disclosure. In one example, the computing device is computing device 1110.

As will be appreciated by those skilled in the art, the techniques of the present disclosure can be readily adapted to computing devices that employ a user-input device other than a touchscreen (e.g., a mouse/cursor system for a conventional, non-touch screen, in user clicks correspond to presses; a stylus/trackpad system; etc.), and it will be clear to those skilled in the art, after reading this disclosure, how to make and use such alternative embodiments.

It is to be understood that the disclosure teaches just some exemplary embodiments and that many variations of the invention can easily be devised by those skilled in the art after reading this disclosure and that the scope of the present invention is to be determined by the following claims.

What is claimed is:

1. A method comprising:
   displaying, via a touch screen of a computing device, a three-quarter view of a plurality of icons arranged in a ring, wherein each of the icons is associated with a respective parameter related to one or both of health and fitness;
   receiving, via the touch screen, a left-to-right swiping gesture by a user of the computing device who is wearing a wearable device;
   displaying via the touch screen, in response to the left-to-right swiping gesture, a counter-clockwise rotation of the ring of icons;
   receiving, via the touch screen, a first press of a first icon of the plurality of icons that lasts for less than N units of time, wherein N is a positive real number;
   displaying via the touch screen, in response to the first press of the first icon, historical data for the parameter associated with the first icon, wherein the historical data is associated with the user and is based on one or more prior measurements taken by the wearable device and transmitted to the computing device;
   receiving, via the touch screen, a second press of the first icon that lasts for at least N units of time and at most M units of time, wherein M is a positive real number greater than N; and
   transmitting by the computing device, in response to the second press of the first icon, a request to the wearable device to (1) take one or more new measurements of the parameter associated with the first icon, and (2) transmit the one or more new measurements to the computing device.

2. The method of claim 1 further comprising displaying via the touch screen, in response to the second press of the first icon, at least one of the one or more new measurements.

3. The method of claim 1 further comprising processing the one or more new measurements.

4. The method of claim 3 wherein the processing comprises estimating respiratory rate based on heart rate measurements.

5. The method of claim 3 wherein the processing comprises estimating calories burned based on heart rate measurements.

6. The method of claim 1 wherein at least one of the icons is displayed within a respective shape.

7. The method of claim 6 wherein at least one of the respective shapes is a two-dimensional projection of a sphere.

8. The method of claim 6 wherein the respective shape of the first icon is displayed with a fill color that is based on at least one of: (1) the one or more new measurements for the parameter associated with the first icon, or (2) the one or more prior measurements for the parameter associated with the first icon.

9. The method of claim 6 wherein the first icon is displayed with a color that is based on at least one of: (1) the one or more new measurements for the parameter associated with the first icon, or (2) the one or more prior measurements for the parameter associated with the first icon.

10. The method of claim 1 further comprising displaying a wellness score that is based on measurements of a plurality of parameters.

11. A method comprising:
    displaying, via a touch screen of a computing device, a three-quarter view of a plurality of icons arranged in a ring, wherein each of the icons is associated with a respective parameter related to one or both of health and fitness;
    receiving, via the touch screen, a right-to-left swiping gesture by a user of the computing device who is wearing a wearable device;
    displaying via the touch screen, in response to the right-to-left swiping gesture, a clockwise rotation of the ring of icons;
    receiving, via the touch screen, a first press of a first icon of the plurality of icons that lasts for less than N units of time, wherein N is a positive real number;
    displaying via the touch screen, in response to the first press of the first icon, historical data for the parameter associated with the first icon, wherein the historical data is associated with the user and is based on one or more prior measurements taken by the wearable device and transmitted to the computing device;
    receiving, via the touch screen, a second press of the first icon that lasts for at least N units of time and at most M units of time, wherein M is a positive real number greater than N; and
    transmitting by the computing device, in response to the second press of the first icon, a request to the wearable device to (1) take one or more new measurements of the parameter associated with the first icon, and (2) transmit the one or more new measurements to the computing device.

12. The method of claim 11 further comprising displaying via the touch screen, in response to the second press of the first icon, at least one of the one or more new measurements.

13. The method of claim 11 further comprising processing the one or more new measurements.

14. The method of claim 13 wherein the processing comprises estimating respiratory rate based on heart rate measurements.

15. The method of claim 13 wherein the processing comprises estimating calories burned based on heart rate measurements.

16. The method of claim 11 wherein at least one of the icons is displayed within a respective shape.

17. The method of claim 16 wherein at least one of the respective shapes is a two-dimensional projection of a sphere.

18. The method of claim 16 wherein the respective shape of the first icon is displayed with a fill color that is based on at least one of: (1) the one or more new measurements for the parameter associated with the first icon, or (2) the one or more prior measurements for the parameter associated with the first icon.

19. The method of claim 18 wherein a green fill color for the respective shape of the first icon is associated with a normal range for the parameter associated with the first icon, and wherein a red fill color for the respective shape of the first icon is associated with an abnormal range for the parameter associated with the first icon.

20. The method of claim 16 wherein the first icon is displayed with a color that is based on at least one of: (1) the one or more new measurements for the parameter associated with the first icon, or (2) the one or more prior measurements for the parameter associated with the first icon.

* * * * *